(12) United States Patent
Weisburg et al.

(10) Patent No.: US 7,381,811 B2
(45) Date of Patent: Jun. 3, 2008

(54) **COMPOSITIONS AND METHODS FOR DETECTING *TRICHOMONAS VAGINALIS* IN A SAMPLE**

(75) Inventors: William G. Weisburg, San Diego, CA (US); Jennifer J. Bungo, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 244 days.

(21) Appl. No.: 10/848,922

(22) Filed: May 18, 2004

(65) Prior Publication Data

US 2004/0235138 A1   Nov. 25, 2004

Related U.S. Application Data

(60) Provisional application No. 60/472,028, filed on May 19, 2003.

(51) Int. Cl.
   *C07H 21/02* (2006.01)
   *C12Q 1/68* (2006.01)
(52) U.S. Cl. .......................... 536/23.1; 435/6
(58) Field of Classification Search ............... 536/23.1; 435/6
   See application file for complete search history.

(56) References Cited

U.S. PATENT DOCUMENTS

| | | |
|---|---|---|
| 5,030,557 A | 7/1991 | Hogan et al. |
| 5,185,439 A | 2/1993 | Arnold, Jr. et al. |
| 5,288,611 A | 2/1994 | Kohne |
| 5,399,491 A | 3/1995 | Kacian et al. |
| 5,654,418 A | 8/1997 | Sheiness et al. |
| 5,985,563 A | 11/1999 | Hyldig-Nielsen et al. |
| 6,130,038 A | 10/2000 | Becker et al. |
| 6,150,517 A | 11/2000 | Hogan et al. |
| 6,361,945 B1 | 3/2002 | Becker et al. |

FOREIGN PATENT DOCUMENTS

WO   WO89/04876 A1   6/1989

OTHER PUBLICATIONS

Brown et al., "Evaluation of the Affirm Ambient Temperature Transport System for the Detection and Identification of *Trichomonas vaginalis, Gardnerella vaginalis*, and *Candida* Species from Vaginal Fluid Specimens," J. Clin. Microbiol., Sep. 2001, 39(9):3197-3199, ASM, USA.

Cotch et al., "*Trichomonas vaginalis* Associated With Low Birth Weight and Preterm Delivery," Sex. Transm. Dis., Jul. 1997, 24(6):353-360, Lippincott, USA.

Cu-Uvin et al., "Prevalence, Incidence, and Persistence or Recurrence of Trichomoniasis among Human Immunodeficiency Virus (HIV)-Positive Women and among HIV-Negative Women at High Risk for HIV Infection," Clin. Infect. Dis., May 2002, 34:1406-1411, The University of Chicago Press, USA.

Garcia, "Protozoa from Other Body Sites," Diagnostic Medical Parasitology, 2001, 4th ed., pp. 120-131, ASM Press, USA.

Gen-Bank Accession No. U17510, "*Trichomonas vaginalis* 16S-like rRNA gene," Nov. 30, 1995.

Gunderson et al., "Phylogeny of Trichomonads Inferred from Small-Subunit rRNA Sequences," J. Euk. Microbiol., Jul.-Aug. 1995, 42(4):411-415, Society of Protozoologists, USA.

Jordan et al., "TaqMan-Based Detection of *Trichomonas vaginalis* DNA from Female Genital Specimens," J. Clin. Microbiol., Nov. 2001, 39(11):3819-3822, ASM, USA.

Kaydos et al., "Development and Validation of a PCR-Based Enzyme-Linked Immunosorbent Assay with Urine for Use in Clinical Research Settings to Detect *Trichomonas vaginalis* in Women," J. Clin. Microbiol., Jan. 2002, 40(1):89-95, ASM, USA.

Kikuta et al., "Specific and sensitive detection of *Trichomonas tenax* by the polymerase chain reaction," Lett. Appl. Microbiol., 24:193-197, The Society for Applied Bacteriology, Blackwell Publishing, UK, 1997.

Krieger et al., "Diagnosis of Trichomoniasis—Comparison of Conventional Wet-Mount Examination With Cytologic Studies, Cultures, and Monoclonal Antibody Staining of Direct Specimens," JAMA, Feb. 1988, 259(8):1223-1227, American Medical Association, USA.

Leber et al., "Intestinal and Urogenital Amebae, Flagellates, and Ciliates," Manual of Clinical Microbiology, 7th ed., 1999, pp. 1391-1405, ASM Press, USA.

Mayata et al., "18S Ribosomal DNA-Based PCR for Diagnosis of *Trichomonas vaginalis*," J. Clin. Microbiol., Jul. 2000, 38(7):2683-2687, ASM, USA.

Niccolai et al., "Incidence and Predictors of Reinfection with *Trichomonas vaginalis* in HIV-infected Women," Sex. Transm. Dis., May 2000, 27(5):284-288, Lippincott, USA.

Rein, "*Trichomonas vaginalis*," Principles and Practice of Infectious Diseases, 5th ed., 2000, pp. 2894-2898, Churchill Livingstone, USA.

Sorvillo et al., "*Trichomonas vaginalis*, HIV, and African-Americans," Emerg. Infect. Dis., Nov.-Dec. 2001, 7(6):927-932, CDC, USA.

Sorvillo et al., "Risk Factors for Trichomoniasis Among Women With Human Immunodeficiency Virus (HIV) Infection at a Public Clinic in Los Angeles County, California: Implications for HIV Prevention," Am. J. Trop. Med. Hyg., 1998, 58(4):495-500, The American Society of Tropical Medicine and Hygiene, USA.

(Continued)

*Primary Examiner*—Mark Navarro
(74) *Attorney, Agent, or Firm*—Charles B. Cappellari

(57) ABSTRACT

The present invention relates to oligonucleotides useful for determining the presence of *Trichomonas vaginalis* in a test sample. The oligonucleotides of the present invention may be incorporated into detection probes, helper probes, capture probes and amplification oligonucleotides, and used in various combinations thereof.

41 Claims, No Drawings

OTHER PUBLICATIONS

Ter Kuile et al., "Influence of growth conditions on RNA levels in relation to activity of core metabolic enzymes in the parasitic protests *Trypanosoma brucei* and *Trichomonas vaginalis*," Microbiol., 1999, 145:755-765, SGM, UK.

Van Der Schee et al., "Improved Diagnosis of *Trichomonas vaginalis* Infection by PCR Using Vaginal Swabs and Urine Specimens Compared to Diagnosis by Wet Mount Microscopy, Culture, and Fluorescent Staining," J. Clin. Microbiol., Dec. 1999, 37(12):4127-4130, ASM, USA.

Wendel et al., "*Trichomonas vaginalis* Polymerase Chain Reaction Compared with Standard Diagnostic and Therapeutic Protocols for Detection and Treatment of Vaginal Trichomoniasis," Clin. Infect. Dis., Sep. 2002, 35:576-580, The University of Chicago Press, USA.

PCT Written Opinion of the International Searching Authority for International Application No. PCT/US2004/015742, dated Aug. 10, 2005.

PCT Search Report, International Application No. PCT/US04/015742, Aug. 10, 2005.

EPO Office Action, European Patent Application No. 04809385.0, Dec. 18, 2006.

SEQUENCE LISTING

<160> NUMBER OF SEQ ID NOS: 105

<210> SEQ ID NO 1
<211> LENGTH: 32
<212> TYPE: DNA
<213> ORGANISM: Trichomonas vaginalis

<400> SEQUENCE: 1
gccgaagtcc ttcggttaaa gttctaattg gg                      32

<210> SEQ ID NO 2
<211> LENGTH: 32
<212> TYPE: RNA
<213> ORGANISM: Trichomonas vaginalis

<400> SEQUENCE: 2
gccgaagucc uucgguuaaa guucuaauug gg                      32

<210> SEQ ID NO 3
<211> LENGTH: 32
<212> TYPE: DNA
<213> ORGANISM: Trichomonas vaginalis

<400> SEQUENCE: 3
cccaattaga actttaaccg aaggacttcg gc                      32

<210> SEQ ID NO 4
<211> LENGTH: 32
<212> TYPE: RNA
<213> ORGANISM: Artificial
<220> FEATURE:
<223> OTHER INFORMATION: RNA equivalent of Trichomonas vaginalis DNA

<400> SEQUENCE: 4
cccaauuaga acuuuaaccg aaggacuucg gc                      32

<210> SEQ ID NO 5
<211> LENGTH: 30
<212> TYPE: DNA
<213> ORGANISM: Trichomonas vaginalis

<400> SEQUENCE: 5
ccattggtgc cttttggtac tgtggatagg                         30

<210> SEQ ID NO 6
<211> LENGTH: 30
<212> TYPE: RNA
<213> ORGANISM: Trichomonas vaginalis

<400> SEQUENCE: 6
ccauuggugc cuuuugguac uguggauagg                         30

<210> SEQ ID NO 7
<211> LENGTH: 30
<212> TYPE: DNA
<213> ORGANISM: Trichomonas vaginalis

<400> SEQUENCE: 7
cctatccaca gtaccaaaag gcaccaatgg                         30

<210> SEQ ID NO 8
<211> LENGTH: 30

```
<212> TYPE: RNA
<213> ORGANISM: Artificial
<220> FEATURE:
<223> OTHER INFORMATION: RNA equivalent of Trichomonas vaginalis DNA

<400> SEQUENCE: 8 ccauccaca guaccaaaag gcaccaaugg                                    30

<210> SEQ ID NO 9
<211> LENGTH: 26
<212> TYPE: DNA
<213> ORGANISM: Trichomonas vaginalis

<400> SEQUENCE: 9
ttccattggt gccttttggt actgtg                                       26

<210> SEQ ID NO 10
<211> LENGTH: 26
<212> TYPE: RNA
<213> ORGANISM: Trichomonas vaginalis

<400> SEQUENCE: 10
uuccauuggu gccuuuggu acugug                                        26

<210> SEQ ID NO 11
<211> LENGTH: 26
<212> TYPE: DNA
<213> ORGANISM: Trichomonas vaginalis

<400> SEQUENCE: 11
cacagtacca aaaggcacca atgaa                                        26

<210> SEQ ID NO 12
<211> LENGTH: 26
<212> TYPE: RNA
<213> ORGANISM: Artificial
<220> FEATURE:
<223> OTHER INFORMATION: RNA equivalent of Trichomonas vaginalis DNA

<400> SEQUENCE: 12
cacaguacca aaaggcacca auggaa                                       26

<210> SEQ ID NO 13
<211> LENGTH: 27
<212> TYPE: DNA
<213> ORGANISM: Trichomonas vaginalis

<400> SEQUENCE: 13
ccattggtgc cttttggtac tgtggat                                      27

<210> SEQ ID NO 14
<211> LENGTH: 27
<212> TYPE: RNA
<213> ORGANISM: Trichomonas vaginalis

<400> SEQUENCE: 14
ccauuggugc cuuuugguac uguggau                                      27

<210> SEQ ID NO 15
<211> LENGTH: 27
<212> TYPE: DNA
<213> ORGANISM: Trichomonas vaginalis

<400> SEQUENCE: 15
```
atccacagta ccaaaaggca ccaatgg        27

<210> SEQ ID NO 16
<211> LENGTH: 27
<212> TYPE: RNA
<213> ORGANISM: Artificial
<220> FEATURE:
<223> OTHER INFORMATION: RNA equivalent of Trichomonas vaginalis DNA

<400> SEQUENCE: 16
auccacagua ccaaaaggca ccaaugg        27

<210> SEQ ID NO 17
<211> LENGTH: 24
<212> TYPE: DNA
<213> ORGANISM: Trichomonas vaginalis

<400> SEQUENCE: 17
ccattggtgc cttttggtac tgtg        24

<210> SEQ ID NO 18
<211> LENGTH: 24
<212> TYPE: RNA
<213> ORGANISM: Trichomonas vaginalis

<400> SEQUENCE: 18
ccauuggugc cuuuugguac ugug        24

<210> SEQ ID NO 19
<211> LENGTH: 24
<212> TYPE: DNA
<213> ORGANISM: Trichomonas vaginalis

<400> SEQUENCE: 19
cacagtacca aaaggcacca atgg        24

<210> SEQ ID NO 20
<211> LENGTH: 24
<212> TYPE: RNA
<213> ORGANISM: Artificial
<220> FEATURE:
<223> OTHER INFORMATION: RNA equivalent of Trichomonas vaginalis DNA

<400> SEQUENCE: 20
cacaguacca aaaggcacca augg        24

<210> SEQ ID NO 21
<211> LENGTH: 35
<212> TYPE: DNA
<213> ORGANISM: Trichomonas vaginalis

<400> SEQUENCE: 21
gctaacgagc gagattatcg ccaattattt acttt        35

<210> SEQ ID NO 22
<211> LENGTH: 35
<212> TYPE: RNA
<213> ORGANISM: Trichomonas vaginalis

<400> SEQUENCE: 22
gcuaacgagc gagauuaucg ccaauuauuu acuuu        35

<210> SEQ ID NO 23
<211> LENGTH: 35

```
<212> TYPE: DNA
<213> ORGANISM: Trichomonas vaginalis

<400> SEQUENCE: 23
aaagtaaata attggcgata atctcgctcg ttagc                              35

<210> SEQ ID NO 24
<211> LENGTH: 35
<212> TYPE: RNA
<213> ORGANISM: Artificial
<220> FEATURE:
<223> OTHER INFORMATION: RNA equivalent of Trichomonas vaginalis DNA

<400> SEQUENCE: 24
aaaguaaaua auggcgaua aucucgcucg uuagc                              35

<210> SEQ ID NO 25
<211> LENGTH: 30
<212> TYPE: DNA
<213> ORGANISM: Trichomonas vaginalis

<400> SEQUENCE: 25
actccctgcg attttagcag gtggaagagg                                    30

<210> SEQ ID NO 26
<211> LENGTH: 30
<212> TYPE: RNA
<213> ORGANISM: Trichomonas vaginalis

<400> SEQUENCE: 26
acucccugcg auuuuagcag guggaagagg                                    30

<210> SEQ ID NO 27
<211> LENGTH: 30
<212> TYPE: DNA
<213> ORGANISM: Trichomonas vaginalis

<400> SEQUENCE: 27
cctcttccac ctgctaaaat cgcagggagt                                    30

<210> SEQ ID NO 28
<211> LENGTH: 30
<212> TYPE: RNA
<213> ORGANISM: Artificial
<220> FEATURE:
<223> OTHER INFORMATION: RNA equivalent of Trichomonas vaginalis DNA

<400> SEQUENCE: 28
ccucuuccac cugcuaaaau cgcagggagu                                    30

<210> SEQ ID NO 29
<211> LENGTH: 22
<212> TYPE: DNA
<213> ORGANISM: Trichomonas vaginalis

<400> SEQUENCE: 29
atatccacgg gtagcagcag gc                                            22

<210> SEQ ID NO 30
<211> LENGTH: 22
<212> TYPE: RNA
<213> ORGANISM: Trichomonas vaginalis

<400> SEQUENCE: 30
```
auauccacgg guagcagcag gc                                              22

<210> SEQ ID NO 31
<211> LENGTH: 22
<212> TYPE: DNA
<213> ORGANISM: Trichomonas vaginalis

<400> SEQUENCE: 31
gcctgctgct acccgtggat at                                              22

<210> SEQ ID NO 32
<211> LENGTH: 22
<212> TYPE: RNA
<213> ORGANISM: Artificial
<220> FEATURE:
<223> OTHER INFORMATION: RNA equivalent of Trichomonas vaginalis DNA

<400> SEQUENCE: 32
gccugcugcu acccguggau au                                              22

<210> SEQ ID NO 33
<211> LENGTH: 33
<212> TYPE: DNA
<213> ORGANISM: Trichomonas vaginalis

<400> SEQUENCE: 33
gcgttgattc agctaacgag cgagattatc gcc                                  33

<210> SEQ ID NO 34
<211> LENGTH: 33
<212> TYPE: RNA
<213> ORGANISM: Trichomonas vaginalis

<400> SEQUENCE: 34
gcguugauuc agcuaacgag cgagauuauc gcc                                  33

<210> SEQ ID NO 35
<211> LENGTH: 33
<212> TYPE: DNA
<213> ORGANISM: Trichomonas vaginalis

<400> SEQUENCE: 35
ggcgataatc tcgctcgtta gctgaatcaa cgc                                  33

<210> SEQ ID NO 36
<211> LENGTH: 33
<212> TYPE: RNA
<213> ORGANISM: Artificial
<220> FEATURE:
<223> OTHER INFORMATION: RNA equivalent of Trichomonas vaginalis DNA

<400> SEQUENCE: 36
ggcgauaauc ucgcucguua gcugaaucaa cgc                                  33

<210> SEQ ID NO 37
<211> LENGTH: 50
<212> TYPE: DNA
<213> ORGANISM: Trichomonas vaginalis

<400> SEQUENCE: 37
ctgcgatttt agcaggtgga agagggtagc aataacaggt ccgtgatgcc                50

<210> SEQ ID NO 38
<211> LENGTH: 50

```
<212> TYPE: RNA
<213> ORGANISM: Trichomonas vaginalis

<400> SEQUENCE: 38
cugcgauuuu agcaggugga agaggguagc aauaacaggu ccgugaugcc            50

<210> SEQ ID NO 39
<211> LENGTH: 50
<212> TYPE: DNA
<213> ORGANISM: Trichomonas vaginalis

<400> SEQUENCE: 39
ggcatcacgg acctgttatt gctaccctct tccacctgct aaaatcgcag            50

<210> SEQ ID NO 40
<211> LENGTH: 50
<212> TYPE: RNA
<213> ORGANISM: Artificial
<220> FEATURE:
<223> OTHER INFORMATION: RNA equivalent of Trichomonas vaginalis DNA

<400> SEQUENCE: 40
ggcaucacgg accuguuauu gcuacccucu uccaccugcu aaaaucgcag            50

<210> SEQ ID NO 41
<211> LENGTH: 22
<212> TYPE: DNA
<213> ORGANISM: Trichomonas vaginalis

<400> SEQUENCE: 41
gcgttgattc agctaacgag cg                                          22

<210> SEQ ID NO 42
<211> LENGTH: 22
<212> TYPE: RNA
<213> ORGANISM: Trichomonas vaginalis

<400> SEQUENCE: 42
gcguugauuc agcuaacgag cg                                          22

<210> SEQ ID NO 43
<211> LENGTH: 22
<212> TYPE: DNA
<213> ORGANISM: Trichomonas vaginalis

<400> SEQUENCE: 43
cgctcgttag ctgaatcaac gc                                          22

<210> SEQ ID NO 44
<211> LENGTH: 22
<212> TYPE: RNA
<213> ORGANISM: Artificial
<220> FEATURE:
<223> OTHER INFORMATION: RNA equivalent of Trichomonas vaginalis DNA

<400> SEQUENCE: 44
cgcucguuag cugaaucaac gc                                          22

<210> SEQ ID NO 45
<211> LENGTH: 22
<212> TYPE: DNA
<213> ORGANISM: Trichomonas vaginalis

<400> SEQUENCE: 45
```

-continued

| gctaacgagc gagattatcg cc | 22 |

<210> SEQ ID NO 46
<211> LENGTH: 22
<212> TYPE: RNA
<213> ORGANISM: Trichomonas vaginalis

<400> SEQUENCE: 46

| gcuaacgagc gagauuaucg cc | 22 |

<210> SEQ ID NO 47
<211> LENGTH: 22
<212> TYPE: DNA
<213> ORGANISM: Trichomonas vaginalis

<400> SEQUENCE: 47

| ggcgataatc tcgctcgtta gc | 22 |

<210> SEQ ID NO 48
<211> LENGTH: 22
<212> TYPE: RNA
<213> ORGANISM: Artificial
<220> FEATURE:
<223> OTHER INFORMATION: RNA equivalent of Trichomonas vaginalis DNA

<400> SEQUENCE: 48

| ggcgauaauc ucgcucguua gc | 22 |

<210> SEQ ID NO 49
<211> LENGTH: 25
<212> TYPE: DNA
<213> ORGANISM: Trichomonas vaginalis

<400> SEQUENCE: 49

| ctgcgatttt agcaggtgga agagg | 25 |

<210> SEQ ID NO 50
<211> LENGTH: 25
<212> TYPE: RNA
<213> ORGANISM: Trichomonas vaginalis

<400> SEQUENCE: 50

| cugcgauuuu agcaggugga agagg | 25 |

<210> SEQ ID NO 51
<211> LENGTH: 25
<212> TYPE: DNA
<213> ORGANISM: Trichomonas vaginalis

<400> SEQUENCE: 51

| cctcttccac ctgctaaaat cgcag | 25 |

<210> SEQ ID NO 52
<211> LENGTH: 25
<212> TYPE: RNA
<213> ORGANISM: Artificial
<220> FEATURE:
<223> OTHER INFORMATION: RNA equivalent of Trichomonas vaginalis DNA

<400> SEQUENCE: 52

| ccucuuccac cugcuaaaau cgcag | 25 |

<210> SEQ ID NO 53
<211> LENGTH: 22

```
<212> TYPE: DNA
<213> ORGANISM: Trichomonas vaginalis

<400> SEQUENCE: 53
gcaataacag gtccgtgatg cc                                              22

<210> SEQ ID NO 54
<211> LENGTH: 22
<212> TYPE: RNA
<213> ORGANISM: Trichomonas vaginalis

<400> SEQUENCE: 54
gcaauaacag guccgugaug cc                                              22

<210> SEQ ID NO 55
<211> LENGTH: 22
<212> TYPE: DNA
<213> ORGANISM: Trichomonas vaginalis

<400> SEQUENCE: 55
ggcatcacgg acctgttatt gc                                              22

<210> SEQ ID NO 56
<211> LENGTH: 22
<212> TYPE: RNA
<213> ORGANISM: Artificial
<220> FEATURE:
<223> OTHER INFORMATION: RNA equivalent of Trichomonas vaginalis DNA

<400> SEQUENCE: 56
ggcaucacgg accuguuauu gc                                              22

<210> SEQ ID NO 57
<211> LENGTH: 51
<212> TYPE: DNA
<213> ORGANISM: Trichomonas vaginalis

<400> SEQUENCE: 57
ggtagcagca ggcgcgaaac tttcccactc gagactttcg gaggaggtaa t              51

<210> SEQ ID NO 58
<211> LENGTH: 51
<212> TYPE: RNA
<213> ORGANISM: Trichomonas vaginalis

<400> SEQUENCE: 58
gguagcagca ggcgcgaaac uuucccacuc gagacuuucg gaggagguaa u              51

<210> SEQ ID NO 59
<211> LENGTH: 51
<212> TYPE: DNA
<213> ORGANISM: Trichomonas vaginalis

<400> SEQUENCE: 59
attacctcct ccgaaagtct cgagtgggaa agtttcgcgc ctgctgctac c              51

<210> SEQ ID NO 60
<211> LENGTH: 51
<212> TYPE: RNA
<213> ORGANISM: Artificial
<220> FEATURE:
<223> OTHER INFORMATION: RNA equivalent of Trichomonas vaginalis DNA

<400> SEQUENCE: 60
```
auuaccuccu ccgaaagucu cgagugggaa aguuucgcgc cugcugcuac c        51

```
<210> SEQ ID NO 61
<211> LENGTH: 43
<212> TYPE: DNA
<213> ORGANISM: Trichomonas vaginalis

<400> SEQUENCE: 61
```
accgtaccga aacctagcag agggccagtc tggtgccagc agc        43

```
<210> SEQ ID NO 62
<211> LENGTH: 43
<212> TYPE: RNA
<213> ORGANISM: Trichomonas vaginalis

<400> SEQUENCE: 62
```
accguaccga aaccuagcag agggccaguc uggugccagc agc        43

```
<210> SEQ ID NO 63
<211> LENGTH: 43
<212> TYPE: DNA
<213> ORGANISM: Trichomonas vaginalis

<400> SEQUENCE: 63
```
gctgctggca ccagactggc cctctgctag gtttcggtac ggt        43

```
<210> SEQ ID NO 64
<211> LENGTH: 43
<212> TYPE: RNA
<213> ORGANISM: Artificial
<220> FEATURE:
<223> OTHER INFORMATION: RNA equivalent of Trichomonas vaginalis DNA

<400> SEQUENCE: 64
```
gcugcuggca ccagacuggc ccucugcuag guuucgguac ggu        43

```
<210> SEQ ID NO 65
<211> LENGTH: 16
<212> TYPE: DNA
<213> ORGANISM: Trichomonas vaginalis

<400> SEQUENCE: 65
```
ggtagcagca ggcgcg        16

```
<210> SEQ ID NO 66
<211> LENGTH: 16
<212> TYPE: RNA
<213> ORGANISM: Trichomonas vaginalis

<400> SEQUENCE: 66
```
gguagcagca ggcgcg        16

```
<210> SEQ ID NO 67
<211> LENGTH: 16
<212> TYPE: DNA
<213> ORGANISM: Trichomonas vaginalis

<400> SEQUENCE: 67
```
cgcgcctgct gctacc        16

```
<210> SEQ ID NO 68
<211> LENGTH: 16
<212> TYPE: RNA
<213> ORGANISM: Artificial
```

```
<220> FEATURE:
<223> OTHER INFORMATION: RNA equivalent of Trichomonas vaginalis DNA

<400> SEQUENCE: 68
cgcgccugcu gcuacc                                                        16

<210> SEQ ID NO 69
<211> LENGTH: 20
<212> TYPE: DNA
<213> ORGANISM: Trichomonas vaginalis

<400> SEQUENCE: 69
ccactcgaga ctttcggagg                                                    20

<210> SEQ ID NO 70
<211> LENGTH: 20
<212> TYPE: RNA
<213> ORGANISM: Trichomonas vaginalis

<400> SEQUENCE: 70
ccacucgaga cuuucggagg                                                    20

<210> SEQ ID NO 71
<211> LENGTH: 20
<212> TYPE: DNA
<213> ORGANISM: Trichomonas vaginalis

<400> SEQUENCE: 71
cctccgaaag tctcgagtgg                                                    20

<210> SEQ ID NO 72
<211> LENGTH: 20
<212> TYPE: RNA
<213> ORGANISM: Artificial
<220> FEATURE:
<223> OTHER INFORMATION: RNA equivalent of Trichomonas vaginalis DNA

<400> SEQUENCE: 72
ccuccgaaag ucucgagugg                                                    20

<210> SEQ ID NO 73
<211> LENGTH: 21
<212> TYPE: DNA
<213> ORGANISM: Trichomonas vaginalis

<400> SEQUENCE: 73
gagactttcg gaggaggtaa t                                                  21

<210> SEQ ID NO 74
<211> LENGTH: 21
<212> TYPE: RNA
<213> ORGANISM: Trichomonas vaginalis

<400> SEQUENCE: 74
gagacuuucg gaggagguaa u                                                  21

<210> SEQ ID NO 75
<211> LENGTH: 21
<212> TYPE: DNA
<213> ORGANISM: Trichomonas vaginalis

<400> SEQUENCE: 75
attacctcct ccgaaagtct c                                                  21
```

<210> SEQ ID NO 76
<211> LENGTH: 21
<212> TYPE: RNA
<213> ORGANISM: Artificial
<220> FEATURE:
<223> OTHER INFORMATION: RNA equivalent of Trichomonas vaginalis DNA

<400> SEQUENCE: 76
auuaccuccu ccgaaagucu c                                    21

<210> SEQ ID NO 77
<211> LENGTH: 23
<212> TYPE: DNA
<213> ORGANISM: Trichomonas vaginalis

<400> SEQUENCE: 77
accgtaccga aacctagcag agg                                  23

<210> SEQ ID NO 78
<211> LENGTH: 23
<212> TYPE: RNA
<213> ORGANISM: Trichomonas vaginalis

<400> SEQUENCE: 78
accguaccga aaccuagcag agg                                  23

<210> SEQ ID NO 79
<211> LENGTH: 23
<212> TYPE: DNA
<213> ORGANISM: Trichomonas vaginalis

<400> SEQUENCE: 79
cctctgctag gtttcggtac ggt                                  23

<210> SEQ ID NO 80
<211> LENGTH: 23
<212> TYPE: RNA
<213> ORGANISM: Artificial
<220> FEATURE:
<223> OTHER INFORMATION: RNA equivalent of Trichomonas vaginalis DNA

<400> SEQUENCE: 80
ccucugcuag guuucgguac ggu                                  23

<210> SEQ ID NO 81
<211> LENGTH: 23
<212> TYPE: DNA
<213> ORGANISM: Trichomonas vaginalis

<400> SEQUENCE: 81
cgaaacctag cagagggcca gtc                                  23

<210> SEQ ID NO 82
<211> LENGTH: 23
<212> TYPE: RNA
<213> ORGANISM: Trichomonas vaginalis

<400> SEQUENCE: 82
cgaaaccuag cagagggcca guc                                  23

<210> SEQ ID NO 83
<211> LENGTH: 23
<212> TYPE: DNA
<213> ORGANISM: Trichomonas vaginalis

<400> SEQUENCE: 83
gactggccct ctgctaggtt tcg                                                 23

<210> SEQ ID NO 84
<211> LENGTH: 23
<212> TYPE: RNA
<213> ORGANISM: Artificial
<220> FEATURE:
<223> OTHER INFORMATION: RNA equivalent of Trichomonas vaginalis DNA

<400> SEQUENCE: 84
gacuggcccu cugcuagguu ucg                                                 23

<210> SEQ ID NO 85
<211> LENGTH: 19
<212> TYPE: DNA
<213> ORGANISM: Trichomonas vaginalis

<400> SEQUENCE: 85
ccagtctggt gccagcagc                                                      19

<210> SEQ ID NO 86
<211> LENGTH: 19
<212> TYPE: RNA
<213> ORGANISM: Trichomonas vaginalis

<400> SEQUENCE: 86
ccagucuggu gccagcagc                                                      19

<210> SEQ ID NO 87
<211> LENGTH: 19
<212> TYPE: DNA
<213> ORGANISM: Trichomonas vaginalis

<400> SEQUENCE: 87
gctgctggca ccagactgg                                                      19

<210> SEQ ID NO 88
<211> LENGTH: 19
<212> TYPE: RNA
<213> ORGANISM: Artificial
<220> FEATURE:
<223> OTHER INFORMATION: RNA equivalent of Trichomonas vaginalis DNA

<400> SEQUENCE: 88
gcugcuggca ccagacugg                                                      19

<210> SEQ ID NO 89
<211> LENGTH: 27
<212> TYPE: DNA
<213> ORGANISM: Artificial
<220> FEATURE:
<223> OTHER INFORMATION: T7 RNA polymerase promoter sequence

<400> SEQUENCE: 89
aatttaatac gactcactat agggaga                                             27

<210> SEQ ID NO 90
<211> LENGTH: 133
<212> TYPE: DNA
<213> ORGANISM: Trichomonas vaginalis

<400> SEQUENCE: 90

```
gcgttgattc agctaacgag cgagattatc gccaattatt tactttgccg aagtccttcg      60
gttaaagttc taattgggac tccctgcgat tttagcaggt ggaagagggt agcaataaca     120
ggtccgtgat gcc                                                        133

<210> SEQ ID NO 91
<211> LENGTH: 133
<212> TYPE: RNA
<213> ORGANISM: Trichomonas vaginalis

<400> SEQUENCE: 91
gcguugauuc agcuaacgag cgagauuauc gccaauuauu acuuugccg aaguccuucg       60 guuaaaguuc uaauugggac ucccugcgau uuuagcaggu ggaagagggu agcaauaaca    120
gguccgugau gcc                                                        133

<210> SEQ ID NO 92
<211> LENGTH: 133
<212> TYPE: DNA
<213> ORGANISM: Trichomonas vaginalis

<400> SEQUENCE: 92
ggcatcacgg acctgttatt gctaccctct tccacctgct aaaatcgcag ggagtcccaa     60
ttagaacttt aaccgaagga cttcggcaaa gtaaataatt ggcgataatc tcgctcgtta    120
gctgaatcaa cgc                                                        133

<210> SEQ ID NO 93
<211> LENGTH: 133
<212> TYPE: RNA
<213> ORGANISM: Artificial
<220> FEATURE:
<223> OTHER INFORMATION: RNA equivalent of Trichomonas vaginalis DNA

<400> SEQUENCE: 93
ggcaucacgg accuguuauu gcucccucu uccaccugcu aaaaucgcag ggaqucccaa       60 uuagaacuuu aaccgaagga cuucggcaaa guaaauaauu ggcgauaauc ucgcucguua    120
gcugaaucaa cgc                                                        133

<210> SEQ ID NO 94
<211> LENGTH: 145
<212> TYPE: DNA
<213> ORGANISM: Trichomonas vaginalis

<400> SEQUENCE: 94
ggtagcagca ggcgcgaaac tttcccactc gagactttcg gaggaggtaa tgaccagttc     60
cattggtgcc ttttggtact gtggataggg gtacggtttt ccaccgtacc gaaacctagc    120
agagggccag tctggtgcca gcagc                                          145

<210> SEQ ID NO 95
<211> LENGTH: 145
<212> TYPE: RNA
<213> ORGANISM: Trichomonas vaginalis

<400> SEQUENCE: 95
gguagcagca ggcgcgaaac uuucccacuc gagacuuucg gaggagguaa ugaccaguuc     60
cauuggugcc uuuugguacu guggauaggg guacgguuuu ccaccguacc gaaaccuagc    120
agagggccag ucuggugcca gcagc                                          145
```

```
<210> SEQ ID NO 96
<211> LENGTH: 145
<212> TYPE: DNA
<213> ORGANISM: Trichomonas vaginalis

<400> SEQUENCE: 96
gctgctggca ccagactggc cctctgctag gtttcggtac ggtggaaaac cgtacccta      60 tccacagtac caaaaggcac caatggaact ggtcattacc tcctccgaaa gtctcgagtg    120
ggaaagtttc gcgcctgctg ctacc                                          145

<210> SEQ ID NO 97
<211> LENGTH: 145
<212> TYPE: RNA
<213> ORGANISM: Artificial
<220> FEATURE:
<223> OTHER INFORMATION: RNA equivalent of Trichomonas vaginalis DNA

<400> SEQUENCE: 97
gcugcuggca ccagacuggc ccucugcuag guuucgguac gguggaaaac cguacccua      60 uccacaguac caaaaggcac caauggaacu ggucauuacc uccuccgaaa gucucgagug    120
ggaaaguuuc gcgccugcug cuacc                                          145

<210> SEQ ID NO 98
<211> LENGTH: 33
<212> TYPE: DNA
<213> ORGANISM: Artificial
<220> FEATURE:
<223> OTHER INFORMATION: Polynucleotide having a 3' poly (dA)30 tail and
      a 5' poly (dT)3 flexible linker for use in a capture probe

<400> SEQUENCE: 98
tttaaaaaaa aaaaaaaaaa aaaaaaaaaa aaa                                  33

<210> SEQ ID NO 99
<211> LENGTH: 55
<212> TYPE: DNA
<213> ORGANISM: Artificial
<220> FEATURE:
<223> OTHER INFORMATION: Capture probe having a 5' region complementary
      to 18S rRNA of Trichomonas vaginalis and a 3' region having a 3'
      poly (dA)14 tail and a 5' poly (dT)3 flexible linker

<400> SEQUENCE: 99
gcctgctgct acccgtggat attttaaaaa aaaaaaaaaa aaaaaaaaaa aaaaa          55

<210> SEQ ID NO 100
<211> LENGTH: 49
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis

<400> SEQUENCE: 100
aatttaatac gactcactat agggagaggc atcacggacc tgttattgc                 49

<210> SEQ ID NO 101
<211> LENGTH: 50
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis
```

```
<400> SEQUENCE: 101
aatttaatac gactcactat agggagacct ctgctaggtt tcggtacggt                    50

<210> SEQ ID NO 102
<211> LENGTH: 50
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis

<400> SEQUENCE: 102
aatttaatac gactcactat agggagagac tggccctctg ctaggtttcg                    50

<210> SEQ ID NO 103
<211> LENGTH: 46
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis

<400> SEQUENCE: 103
aatttaatac gactcactat agggagagct gctggcacca gactgg                        46

<210> SEQ ID NO 104
<211> LENGTH: 52
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis

<400> SEQUENCE: 104
aatttaatac gactcactat agggagacct cttccacctg ctaaaatcgc ag                 52

<210> SEQ ID NO 105
<211> LENGTH: 49
<212> TYPE: DNA
<213> ORGANISM: Artificial
<220> FEATURE:
<223> OTHER INFORMATION: Promoter-primer having a 5' region T7 RNA
      polymerase promoter sequence and a 3' region complementary to 18S
      rRNA of Trichomonas vaginalis

<400> SEQUENCE: 105
aatttaatac gactcactat agggagaggc atcacggacc tgttattgc                     49
```

COMPOSITIONS AND METHODS FOR DETECTING *TRICHOMONAS VAGINALIS* IN A SAMPLE

CROSS-REFERENCE TO RELATED APPLICATIONS

This application claims the benefit of U.S. Provisional Application No. 60/472,028, filed May 19, 2003, the contents of which are hereby incorporated by reference herein in their entirety.

FIELD OF THE INVENTION

The present invention relates to detection probes, helper probes, capture probes, amplification oligonucleotides, nucleic acid compositions, probe mixes, methods, and kits useful for determining the presence of *Trichomonas vaginalis* in a test sample.

BACKGROUND OF THE INVENTION

*Trichomonas vaginalis* is protozoan parasite that causes trichomoniasis, one of the most common and treatable of the sexually transmitted diseases. *Trichomonas vaginalis* is a relatively delicate pear-shaped trophozoite that is typically 7 to 23 µm long by 5 to 12 µm wide. The organism has four anterior flagella and a fifth forming the outer edge of a short undulating membrane. The anterior flagella propels the organism through liquid in a jerky, rapid fashion, sometimes causing the organism to rotate as it moves. *Trichomonas vaginalis* divides by binary fission in the urogenital tract of those infected. The organism is clear, uncolored, or slightly grey in appearance under the microscope. A slender rod, the axostyle, extends the length of the body and protrudes posteriorly. The nucleus is near-anterior and appears well-defined, containing many chromatin granules. The appearance of *T. vaginalis* is very similar to that of other trichomonads, such as *Trichomonas tenax*, although only *T. vaginalis* is found in genitourinary tract infections.

Worldwide, *T. vaginalis* infects approximately 180 million people per year, usually by direct person-to-person contact, making it the most common sexually transmitted disease (STD) agent. In the United States, it is believed that *T. vaginalis* infects an estimated 5 million people annually. Despite its prevalence and geographic distribution, *T. vaginalis* has not been the focus of intensive study. Indeed, it is not even listed as a "reportable disease" by the U.S. Centers for Disease Control, and there are no active control or prevention programs. Recent reports, however, suggest growing public health interest in this pathogen.

Infections in women are known to cause vaginitis, urethritis, and cervicitis. Severe infections are accompanied by a foamy, yellowish-green discharge with a foul odor, and small hemorrhagic lesions may also be present in the genitourinary tract. Complications include premature labor, low-birth weight offspring, premature rupture of membranes, and post-abortion and post-hysterectomy infection. An association with pelvic inflammatory disease, tubal infertility, and cervical cancer have been reported. *Trichomonas vaginalis* has also been implicated as a co-factor in the transmission of HIV and other STD agents. The organism can also be passed to neonates during passage through the birth canal.

In men, symptoms of trichomoniasis include urethral discharge, urethral stricture, epididymitis, the urge to urinate, and a burning sensation with urination. In both men and women, infections with *T vaginalis* are usually asymptomatic and self-limiting. It is estimated that, in women, 10-50% of *T. vaginalis* infections are asymptomatic, with the proportion in men probably being even higher. That said, with many women the infection becomes symptomatic and chronic, with periods of relief in response to therapy. Recurrence may be caused by re-infection from an asymptomatic sexual partner, or by failure of the standard course of therapy (a regimen of the antibiotic metronidazole). And while *T. vaginalis* infections almost always occur in the genitourinary tract, on rare occasions they occur at ecotopic sites, and the parasite may be recovered from other areas of a patient's body.

As a result of suboptimal comparative laboratory methods and a focus on other STD sources, studies of *T. vaginalis* have often substantially underestimated the prevalence of infection. Despite this, levels of infection typically have been high, with reported overall prevalences ranging from 3-58%, with an unweighted average across studies of 21% (Cu-Uvin et al. *Clin. Infect. Dis.* (2002) 34(10):1406-11). In studies that presented information on race/ethnicity, *T. vaginalis* infection rates have been reported to be highest among African-Americans (Sorvillo et al. *Emerg. Infect. Dis.* (2001) 7(6):927-32). The following chart illustrates the trend reported by Sorvillo et al., with regard to the prevalence of infection in terms of the percentage of patients infected with trichomoniasis, chlamydia, and/or gonorrhea at certain health clinics in Baltimore, Md. (B) and in New York, N.Y. (NY).

| Year | Patient Number | City | Trichomoniasis (%) | Chlamydia (%) | Gonorrhea (%) |
| --- | --- | --- | --- | --- | --- |
| 1996 | 213 | NY | 51 | 9 | 5 |
| 1994 | 372 | NY | 27 | 7 | 2 |
| 1994 | 1404 | NY | 20 | 15 | No Data |
| 1992 | 279 | B | 26 | 21 | 14 |
| 1990-94 | 677 | NY | 22 | 6 | 1 |

Following exposure, the incubation period ranges from about 5 to 10 days, although periods as short as 1 day to as many as 28 days have been reported. If diagnosed, *T. vaginalis* infections can be readily treated by orally administered antibiotics.

Given its relative prevalence and association with other STDs, there is increasing interest in effectively diagnosing trichomoniasis. Conventional diagnostic methods for detecting *T. vaginalis*, however, are based on direct examination, "wet mount" microscopy, or cell culture, each of which has its own shortcomings. With regard to direct patient examination, other infections mimic the appearance and odor of the vaginal discharge. Accordingly, laboratory techniques such as microscopy, antibody detection, and cell culture are often used. While it is possible to detect *T. vaginalis* using a "wet mount" prepared by mixing vaginal secretions with saline on a slide and examining the slide under a microscope for the presence of organisms having the characteristic size, shape, and motility of *T. vaginalis*, the sensitivity of such methods depends highly on the skill and experience of the microscopist, as well as the time spent transporting specimen to a laboratory. Wet mount diagnosis has been found to be only 35-80% as sensitive as other methods, such as cell culture, in detecting the presence of *T. vaginalis*. Other direct methods, such as fluorescent antibody detection and enzyme-linked immunoassays, have also been developed, as has a non-amplified, DNA probe-based method (Affirm, Becton Dickinson), although their sensitivities, as compared to cell culture, range from 70-90%. For these reasons, cell culture is considered the current "gold standard" for clinical detection of *T. vaginalis*. Due to its relatively delicate nature, however, the organism is technically challenging, and typically requires up to 7 days for maximum sensitivity. Even then, the sensitivity of cell culture methods is estimated to be only about 85-95% due to problems associated with time lapses between sample recovery and culture inoculation, maintaining proper incubation conditions, visualizing low numbers of the organism and/or the motility of the protozoa.

Given the human health implications of trichomoniasis and relative inability of existing clinical laboratory methods to selectively and sensitively detect *T. vaginalis* from a test sample, a need clearly exists for a sensitive and specific assay which can be used to determine the presence of *T. vaginalis* in a particular sample of biological material.

SUMMARY OF THE INVENTION

The present invention provides a solution to the clinical need for a sensitive assay specific for *T. vaginalis* by featuring oligonucleotides that are useful for determining whether *T. vaginalis* is present in a test sample, such as a genitourinary specimen. The featured oligonucleotides may be contained in detection probes, helper probes, capture probes and/or amplification oligonucleotides that are useful for detecting, immobilizing and/or amplifying *T. vaginalis* target nucleic acid present in a test sample.

In one embodiment, detection probes are provided that can preferentially hybridize to a target region present in nucleic acid derived from *T. vaginalis* to form a detectable probe:target hybrid indicating the presence of *T. vaginalis*. In preferred embodiments, the invention provides a detection probe for determining whether *T. vaginalis* is present in a test sample derived from a biological material, preferably taken from the genitourinary tract of a patient. The detection probe contains a target binding region having an at least 10 contiguous base sequence that is at least about 80%, 90% or 100% complementary to an at least 10 contiguous base region present in a target sequence selected from the group consisting of:

SEQ ID NO:1: gccgaagtccttcggttaaagttctaattggg,

SEQ ID NO:2: gccgaaguccuucgguuaaaguucuaauuggg,

SEQ ID NO:3: cccaattagaactttaaccgaaggacttcggc, and

SEQ ID NO:4: cccaauuagaacuuuaaccgaaggacuucggc.

In another preferred embodiment, the present invention provides a detection probe which contains a target binding region having an at least 10 contiguous base sequence that is at least about 80%, 90% or 100% complementary to an at least 10 contiguous base region present in a target sequence selected from the group consisting of:

SEQ ID NO:5: ccattggtgcctttggtactgtggatagg,

SEQ ID NO:6: ccauuggugccuuuugguacuguggauagg,

SEQ ID NO:7: cctatccacagtaccaaaaggcaccaatgg,

SEQ ID NO:8: ccuauccacaguaccaaaaggcaccaaugg,

SEQ ID NO:9: ttccattggtgcctttggtactgtg,

-continued

SEQ ID NO:10: uuccauuggugccuuuugguacugug,

SEQ ID NO:11: cacagtaccaaaaggcaccaatggaa,

SEQ ID NO:12: cacaguaccaaaaggcaccaauggaa,

SEQ ID NO:13: ccattggtgcctttggtactgtggat,

SEQ ID NO:14: ccauuggugccuuuugguacuguggau,

SEQ ID NO:15: atccacagtaccaaaaggcaccaatgg, and

SEQ ID NO:16: auccacaguaccaaaaggcaccaaugg.

The core region targeted by this preferred detection probe is selected from the group consisting of:

SEQ ID NO:17: ccattggtgcctttggtactgtg,

SEQ ID NO:18: ccauuggugccuuuugguacugug,

SEQ ID NO:19: cacagtaccaaaaggcaccaatgg, and

SEQ ID NO:20: cacaguaccaaaaggcaccaaugg.

Detection probes according to the invention preferentially hybridize to the target nucleic acid and not to nucleic acid derived from non-*T. vaginalis* organisms present in a test sample under stringent hybridization conditions. In particular, the detection probes of the present invention preferentially hybridize to the target nucleic acid and not to nucleic acid derived from *Trichomonas tenax*, which is considered to be the most closely related organism to *T. vaginalis*. *Trichomonas tenax* can be obtained from the American Type Culture Collection in Manassas, Va. as ATCC No. 30207.

In the present invention, the detection probe may have a target binding region of any length suitable to achieve the desired selectivity and specificity for *T. vaginalis*-derived nucleic acid. The base sequence of a detection probe according to the present invention is preferably up to 100 bases in length, more preferably from 10 to 50 bases in length, and most preferably from 18 to 35 bases in length. In a preferred embodiment, the detection probe contains a target binding region having an at least 15 contiguous base sequence which is at least about 80%, 90% or 100% complementary to an at least 15 contiguous base region present in the target sequence. Preferably, the target binding region of the detection probe comprises a base sequence which is fully complementary to the target sequence. More preferably, the base sequence of the target binding region of the detection probe is at least about 80%, 90% or 100% complementary to the target sequence. Most preferably, the base sequence of the detection probe is at least about 80%, 90% or 100% complementary to the target sequence.

The target binding region may consist of deoxyribonucleic acid (DNA), ribonucleic acid (RNA), a combination DNA and RNA, or it may be a nucleic acid analog (e.g., a peptide nucleic acid) or contain one or more modified nucleosides (e.g., a ribonucleoside having a 2'-O-methyl substitution to the ribofuranosyl moiety). The target binding region may additionally include molecules that do not hydrogen bond to adenine, cytosine, guanine, thymine or uracil, provided such molecules do not interfere with the ability of the detection probe to selectively and specifically bind to nucleic acid derived from *T. vaginalis* in the test sample. Such molecules could include, by way of example, abasic nucleotides or universal base analogues, such as 5-nitroindole, provided such molecules do not significantly affect duplex stability. See, e.g., Guo et al., "Artificial Mismatch Hybridization," U.S. Pat. No. 5,780,233, the contents of which are hereby incorporated by reference herein.

A detection probe of the present invention may include one or more base sequences in addition to the base sequence of the target binding region which do not stably bind to nucleic acid derived from *T. vaginalis* under stringent hybridization conditions. An additional base sequence may be comprised of any desired base sequence, so long as it does not stably bind to nucleic acid derived from the *T. vaginalis* under stringent hybridization conditions or prevent stable hybridization of the probe to the target nucleic acid. By way of example, an additional base sequence may constitute the immobilized probe binding region of a capture probe, where the immobilized probe binding region is comprised of, for example, a 3' poly dA (adenine) region which hybridizes under stringent hybridization conditions to a 5' poly dT (thymine) region of a polynucleotide bound directly or indirectly to a solid support. An additional base sequence might also be a 5' sequence recognized by a RNA polymerase or which enhances initiation or elongation by a RNA polymerase (e.g., a T7 promoter). More than one additional base sequence may be included if the first sequence is incorporated into, for example, a self-hybridizing probe (i.e., a probe having distinct base regions capable of hybridizing to each other in the absence of a target sequence under the conditions of an assay), such as a "molecular beacon" probe. Molecular beacons are disclosed by Tyagi et al., "Detectably Labeled Dual Conformation Oligonucleotide Probes, Assays and Kits," U.S. Pat. No. 5,925,517 (the contents of which are hereby incorporated by reference herein), and include a target binding region which is bounded by or overlaps with two base sequences having regions, referred to as "stems" or "arms," which are at least partially complementary to each other. A more detailed description of molecular beacons is provided infra in the section entitled "Detection Probes to *Trichomonas vaginalis* Ribosomal Nucleic Acid." An additional base sequence may be joined directly to the target binding region or, for example, by means of a non-nucleotide linker (e.g., polyethylene glycol or an abasic region).

While not required, detection probes of the present invention preferably include at least one detectable label or group of interacting labels. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester (AE), preferably 4-(2-succinimidyloxycarbonyl ethyl)-phenyl-10-methylacridinium-9-carboxylate fluorosulfanate (hereinafter referred to as "standard AE"). Groups of interacting labels useful with a probe pair (see, e.g., Morrison, "Competitive Homogeneous Assay," U.S. Pat. No. 5,928,862) or a self-hybridizing probe (see, e.g., Tyagi et al., U.S. Pat. No. 5,925,517) include, but are not limited to, enzyme/substrate, enzyme/cofactor, luminescent/quencher, luminescent/adduct, dye dimers and Förrester energy transfer pairs. An interacting luminescent/quencher pair, such as fluoroscein and DABCYL, is particularly preferred.

In a further embodiment, the present invention contemplates probe mixes that are useful for determining whether *T. vaginalis* is present in a test sample. The probe mix may comprise, for example, one of the above-described *T. vaginalis* detection probes and a helper probe. The base sequence of a helper probe according to the present invention is preferably up to 100 bases in length, more preferably from 10 to 50 bases in length, and most preferably from 18 to 35 bases in length. The helper probe preferably contains an at least 10 contiguous base region which is at least about 80%, 90% or 100% complementary to an at least 10 contiguous base region present in a target sequence selected from the group consisting of:

```
SEQ ID NO:21:    gctaacgagcgagattatcgccaattatttactttt,

SEQ ID NO:22:    gcuaacgagcgagauuaucgccaauuauuuacuuu,

SEQ ID NO:23:    aaagtaaataattggcgataatctcgctcgttagc,

SEQ ID NO:24:    aaaguaaauaauuggcgauaaucucgcucguuagc,

SEQ ID NO:25:    actccctgcgattttagcaggtggaagagg,

SEQ ID NO:26:    acucccugcgauuuuagcagguggaagagg,

SEQ ID NO:27:    cctcttccacctgctaaaatcgcagggagt,
and

SEQ ID NO:28:    ccucuuccaccugcuaaaaucgcagggagu.
```

Helper probes according to the present invention need not exhibit specificity for the target sequence in a test sample. In a preferred embodiment, the helper probe comprises an at least 15 contiguous base sequence which is at least about 80%, 90% or 100% complementary to an at least 15 contiguous base region present in the target sequence. Preferably, the helper probe comprises a base sequence which is fully complementary to the target sequence. The base sequence of the helper probe of the present invention is most preferably at least about 80%, 90% or 100% complementary to the target sequence. In a preferred probe mix, the detection probe comprises an at least 10 contiguous base region which is at least about 80% complementary to an at least 10 contiguous base region present in a sequence selected from the group consisting of: SEQ ID NO:1, SEQ ID NO:2, SEQ ID NO:3 and SEQ ID NO:4.

The invention also contemplates compositions comprising stable nucleic acid duplexes formed between any of the above-described detection probes and/or helper probes and the target nucleic acids for the probes under stringent hybridization conditions.

In another embodiment of the present invention, a capture probe is provided for specifically isolating and purifying target nucleic acid derived from *T. vaginalis* present in a test sample. The capture probe includes a target binding region that stably binds to nucleic acid derived from *T. vaginalis* under assay conditions and which has an at least 10 contiguous base region which is at least about 80%, 90% or 100% complementary to an at least 10 contiguous base region present in a target sequence selected from the group consisting of:

```
SEQ ID NO:29:    atatccacgggtagcagcaggc,

SEQ ID NO:30:    auauccacggguagcagcaggc,

SEQ ID NO:31:    gcctgctgctacccgtggatat,
and

SEQ ID NO:32:    gccugcugcuacccguggauau.
```

The base sequence of the target binding region of a capture probe according to the present invention is preferably up to 100 bases in length, more preferably from 10 to 50 bases in length, and most preferably from 18 to 35 bases in length. In a preferred embodiment, the target binding region of the capture probe comprises an at least 15 contiguous base sequence which is at least about 80%, 90% or 100% complementary to an at least 15 contiguous base region present in the target sequence. Preferably, the target binding region of the capture probe comprises a base sequence fully complementary to the target sequence. The base sequence of the target binding region of the capture probe of the present invention is more preferably at least about 80%, 90% or 100% complementary to the target sequence. In a most preferred embodiment, the base sequence of the target binding region of the capture probe is at least about 80%, 90% or 100% complementary to the target sequence, and the capture probe does not include any other base sequences which stably hybridize to nucleic acid derived from *T. vaginalis* under assay conditions.

Capture probes according to the present invention may be immobilized on a solid support by means of ligand-ligate binding pairs, such as avidin-biotin linkages, but preferably include an immobilized probe binding region. The immobilized probe binding region of the preferred capture probes is comprised of any base sequence capable of stably hybridizing under assay conditions to an oligonucleotide that is bound to a solid support present in a test sample. Preferably, the immobilized probe binding region is a poly dA, homopolymer tail positioned at the 3' end of the capture probe. In this embodiment, oligonucleotides bound to the solid support would include 5' poly dT tails of sufficient length to stably bind to the poly dA tails of the capture probes under assay conditions. In a preferred embodiment, the immobilized probe binding region includes a poly dA tail which is about 30 adenines in length, and the capture probe includes a spacer region which is about 3 thymines in length for joining together the target binding region and the immobilized probe binding region.

The present invention also features amplification oligonucleotides useful for determining the presence of *T. vaginalis* in an amplification assay. In a preferred embodiment, the invention provides at least one amplification oligonucleotide for amplifying nucleic acid derived from *T. vaginalis* present in a test sample, where the amplification oligonucleotide has a target binding region that preferably contains an at least 10 contiguous base region which is at least about 80%, 90% or 100% complementary to an at least 10 contiguous base region present in a target sequence selected from the group consisting of:

SEQ ID NO:33: gcgttgattcagctaacgagcgagattatcgcc,

SEQ ID NO:34: gcguugauucagcuaacgagcgagauuaucgcc,

SEQ ID NO:35: ggcgataatctcgctcgttagctgaatcaacgc,

SEQ ID NO:36: ggcgauaaucucgcucguuagcugaaucaacgc,

SEQ ID NO:37: ctgcgattttagcaggtggaagagggtagcaataaca ggtccgtgatgcc,

SEQ ID NO:38: cugcgauuuuagcagguggaagaggguagcaauaaca gguccgugaugcc,

SEQ ID NO:39: ggcatcacggacctgttattgctaccctcttccacct gctaaaatcgcag, and

SEQ ID NO:40: ggcaucacggaccuguuauugcuacccucuuccaccu gcuaaaaucgcag.

More preferably, the target sequence of the amplification oligonucleotide is selected from the group consisting of:

SEQ ID NO:41: gcgttgattcagctaacgagcg,

SEQ ID NO:42: gcguugauucagcuaacgagcg,

SEQ ID NO:43: cgctcgttagctgaatcaacgc,

SEQ ID NO:44: cgcucguuagcugaaucaacgc,

SEQ ID NO:45: gctaacgagcgagattatcgcc,

SEQ ID NO:46: gcuaacgagcgagauuaucgcc,

SEQ ID NO:47: ggcgataatctcgctcgttagc,

SEQ ID NO:48: ggcgauaaucucgcucguuagc,

SEQ ID NO:49: ctgcgattttagcaggtggaagagg,

SEQ ID NO:50: cugcgauuuuagcagguggaagagg,

SEQ ID NO:51: cctcttccacctgctaaaatcgcag,

SEQ ID NO:52: ccucuuccaccugcuaaaaucgcag,

SEQ ID NO:53: gcaataacaggtccgtgatgcc,

SEQ ID NO:54: gcaauaacagguccgugaugcc,

SEQ ID NO:55: ggcatcacggacctgttattgc, and

SEQ ID NO:56: ggcaucacggaccuguuauugc.

In another preferred embodiment, the at least one amplification oligonucleotide for amplifying nucleic acid derived from *T. vaginalis* present in a test sample has a target binding region that preferably contains an at least 10 contiguous base region which is at least about 80%, 90% or 100% complementary to an at least 10 contiguous base region present in a target sequence selected from the group consisting of:

SEQ ID NO:57: ggtagcagcaggcgcgaaactttcccactcgagactt tcggaggaggtaat,

SEQ ID NO:58: gguagcagcaggcgcgaaacuuucccacucgagacuu ucggaggagguaau,

SEQ ID NO:59: attacctcctccgaaagtctcgagtgggaaagtttcg cgcctgctgctacc,

SEQ ID NO:60: auuaccuccuccgaaagucucgagugggaaaguuucg cgccugcugcuacc,

SEQ ID NO:61: accgtaccgaaacctagcagagggccagtctggtgcc agcagc,

SEQ ID NO:62: accguaccgaaaccuagcagagggccagucuggugcc agcagc,

SEQ ID NO:63: gctgctggcaccagactggccctctgctaggtttcgg tacggt, and

-continued

SEQ ID NO:64: gcugcuggcaccagacuggcccucugcuagguuucgg
          uacggu.

More preferably, the target sequence of the amplification oligonucleotide is selected from the group consisting of:

SEQ ID NO:65:    ggtagcagcaggcgcg,

SEQ ID NO:66:    gguagcagcaggcgcg,

SEQ ID NO:67:    cgcgcctgctgctacc,

SEQ ID NO:68:    cgcgccugcugcuacc,

SEQ ID NO:69:    ccactcgagactttcggagg,

SEQ ID NO:70:    ccacucgagacuuucggagg,

SEQ ID NO:71:    cctccgaaagtctcgagtgg,

SEQ ID NO:72:    ccuccgaaagucucgagugg,

SEQ ID NO:73:    gagactttcggaggaggtaat,

SEQ ID NO:74:    gagacuuucggaggagguaau,

SEQ ID NO:75:    attacctcctccgaaagtctc,

SEQ ID NO:76:    auuaccuccuccgaaagucuc,

SEQ ID NO:77:    accgtaccgaaacctagcagagg,

SEQ ID NO:78:    accguaccgaaaccuagcagagg,

SEQ ID NO:79:    cctctgctaggtttcggtacggt,

SEQ ID NO:80:    ccucugcuagguuucgguacggu,

SEQ ID NO:81:    cgaaacctagcagagggccagtc,

SEQ ID NO:82:    cgaaaccuagcagagggccaguc,

SEQ ID NO:83:    gactggccctctgctaggtttcg,

SEQ ID NO:84:    gacuggcccucugcuagguuucg,

SEQ ID NO:85:    ccagtctggtgccagcagc,

SEQ ID NO:86:    ccagucggugccagcagc,

SEQ ID NO:87:    gctgctggcaccagactgg,
and

SEQ ID NO:88:    gcugcuggcaccagacugg.

Amplification oligonucleotides of the present invention have a target binding region that is preferably from 18 to 40 bases in length. In a preferred embodiment, the amplification oligonucleotide contains a target binding region having an at least 15 contiguous base sequence which is at least about 80%, 90% or 100% complementary to an at least 15 contiguous base region present in the target sequence. Preferably, the target binding region of the amplification oligonucleotide comprises a base sequence which is fully complementary to the target sequence. More preferably, the base sequence of the target binding region of the amplification oligonucleotide is at least about 80%, 90% or 100% complementary to the target sequence, and the amplification oligonucleotide does not include any other base sequences which stably hybridize to nucleic acid derived from T. vaginalis under amplification conditions. The amplification oligonucleotide optionally includes a 5' sequence which is recognized by a RNA polymerase or which enhances initiation or elongation by RNA polymerase. The T7 promoter sequence of SEQ ID NO:89: aatttaatacgactcactatagggaga is preferred, although other promoter sequences may be employed.

The invention further contemplates an amplification oligonucleotide which, when contacted with a nucleic acid polymerase under amplification conditions, will bind to or cause extension through a nucleic acid region having a base sequence selected from the group consisting of: SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 and SEQ ID NO:56. In an alternative embodiment, the amplification oligonucleotide binds to or extends through a nucleic acid region having a base sequence selected from the group consisting of: SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID. NO:83, SEQ ID NO:84, SEQ ID NO:85, SEQ ID NO:86, SEQ ID NO:87 and SEQ ID NO:88. The base sequence of an amplification oligonucleotide of such embodiments consists of a target binding region up to 40 bases in length and an optional 5' sequence which is recognized by a RNA polymerase or which enhances initiation or elongation by RNA polymerase (e.g., T7 promoter of SEQ ID NO:89).

Amplification oligonucleotides of the present invention are preferably employed in sets of at least two amplification oligonucleotides. One preferred set includes a first amplification oligonucleotide having a target binding region which contains an at least 10 contiguous base region which is at least about 80% complementary to an at least 10 contiguous base region present in a target sequence selected from the group consisting of: SEQ ID NO:33, SEQ ID NO:34, SEQ ID NO:35 and SEQ ID NO:36. More preferably, the target sequence of the first amplification oligonucleotide is selected from the group consisting of: SEQ ID NO:41, SEQ ID NO:42, SEQ ID NO:43, SEQ ID NO:44, SEQ ID NO:45, SEQ ID NO:46, SEQ ID NO:47 and SEQ ID NO:48. The second amplification oligonucleotide of this preferred set has a target binding region that contains an at least 10 contiguous base region which is at least about 80% complementary to an at least 10 contiguous base region present in a target sequence selected from the group consisting of: SEQ ID NO:37, SEQ ID NO:38, SEQ ID NO:39 and SEQ ID NO:40. More preferably, the target sequence of the second amplification oligonucleotide is selected from the group consisting of: SEQ ID NO:49, SEQ ID NO:50, SEQ ID NO:51, SEQ ID NO:52, SEQ ID NO:53, SEQ ID NO:54, SEQ ID NO:55 and SEQ ID NO:56. Other structural embodiments of the first and second amplification oligonucleotides are those set forth above for individual amplification oligonucleotides. It is preferred that at least one member of the set of amplification oligonucleotides include a 5' sequence which is recognized by a RNA polymerase or which enhances initiation or elongation by RNA polymerase (e.g., T7 promoter of SEQ ID NO:89).

Another set of preferred amplification oligonucleotides includes a first amplification oligonucleotide having a target binding region that contains an at least 10 contiguous base region which is at least about 80% complementary to an at least 10 contiguous base region present in a target sequence selected from the group consisting of: SEQ ID NO:57, SEQ ID NO:58, SEQ ID NO:59 and SEQ ID NO:60. More preferably, the target sequence of the first amplification oligonucleotide is selected from the group consisting of: SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75 and SEQ ID NO:76. The second amplification oligonucleotide of this preferred set has a target binding region that contains an at least 10 contiguous base region which is at least about 80% complementary to an at least 10 contiguous base region present in a target sequence selected from the group consisting of: SEQ ID NO:61, SEQ ID NO:62, SEQ ID NO:63 and SEQ ID NO:64. More preferably, the target sequence of the second amplification oligonucleotide is selected from the group consisting of: SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 and SEQ ID NO:88. Other structural embodiments of the first and second amplification oligonucleotides are those set forth above for individual amplification oligonucleotides. It is preferred that at least one member of the set of amplification oligonucleotides include a 5' sequence which is recognized by a RNA polymerase or which enhances initiation or elongation by RNA polymerase (e.g., T7 promoter of SEQ ID NO:89).

The invention additionally contemplates compositions comprising stable nucleic acid duplexes formed between any of the above-described amplification oligonucleotides and the target nucleic acids for the amplification oligonucleotides under amplification conditions.

In yet another embodiment of the present invention, a set of oligonucleotides is provided for determining the presence of *T. vaginalis* in a test sample, where each member of the set has a target binding region that contains an at least 10 contiguous base region which is at least about 80% complementary to an at least 10 contiguous base region present in a target sequence selected from the group consisting of:

SEQ ID NO:90: gcgttgattcagctaacgagcgagattatcgccaatt
atttactttgccgaagtccttcggttaaagttctaat
tgggactccctgcgattttagcaggtggaagagggta
gcaataacaggtccgtgatgcc, SEQ ID NO:91: gcguugauucagcuaacgagcgagauuaucgccaauu
auuuacuuugccgaaguccuucgguuaaaguucuaau
ugggacucccugcgauuuuagcagguggaagagggua
gcaauaacagguccgugaugcc, SEQ ID NO:92: ggcatcacggacctgttattgctaccctcttccacct
gctaaaatcgcagggagtcccaattagaactttaacc
gaaggacttcggcaaagtaaataattggcgataatct
cgctcgttagctgaatcaacgc,
and SEQ ID NO:93: ggcaucacggaccuguuauugcuacccucuuccaccu
gcuaaaaucgcagggaguccaauuagaacuuuaacc
gaaggacuucggcaaaguaaauaauuggcgauaaucu
cgcucguuagcugaaucaacgc.

In a preferred embodiment, the set of amplification oligonucleotides includes at least one detection probe, preferably one of the above-described detection probes, which preferentially hybridizes to the target sequence and not to nucleic acid derived from non-*T. vaginalis* organisms present in a test sample under stringent hybridization conditions. In another preferred embodiment, the set of oligonucleotides includes at least two oligonucleotides, preferably including one of the above-described detection probes and a helper probe which hybridizes to the target sequence under stringent hybridization conditions, thereby facilitating hybridization of the detection probe to the target sequence, where the helper probe is preferably one of the above-described helper probes. In yet another preferred embodiment, the set of oligonucleotides includes at least three oligonucleotides, preferably including one of the above-described detection probes and a pair of amplification oligonucleotides capable of amplifying all or a portion of the target sequence under amplification conditions, preferably including at least one of the above-described amplification oligonucleotides. And, in a particularly preferred embodiment, each member of the set of oligonucleotides contains an a target binding region which is fully complementary to a sequence contained within the target sequence, and none of the oligonucleotides includes any other base sequences which stably hybridize to nucleic acid derived from *T. vaginalis* under assay conditions.

In still another embodiment of the present invention, a set of oligonucleotides is provided for determining the presence of *T. vaginalis* in a test sample, where each member of the set has a target binding region that contains an at least 10 contiguous base region which is at least about 80% complementary to an at least 10 contiguous base region present in a target sequence selected from the group consisting of:

SEQ ID NO:94: ggtagcagcaggcgcgaaactttcccactcgagact
ttcggaggaggtaatgaccagttccattggtgcctt
ttggtactgtggataggggtacggttttccaccgta
ccgaaacctagcagagggccagtctggtgccagcag
c, SEQ ID NO:95: gguagcagcaggcgcgaaacuuucccacucgagacu
uucggaggagguaaugaccaguuccauuggugccuu
uugguacuguggauaggggucgguuuuccaccgua
ccgaaaccuagcagagggccagucuggugccagcag
c, SEQ ID NO:96: gctgctggcaccagactggccctctgctaggtttcg
gtacggtggaaaaccgtaccccctatccacagtacca
aaaggcaccaatggaactggtcattacctcctccga
aagtctcgagtgggaaagtttcgcgcctgctgctac
c, and SEQ ID NO:97: gcugcuggcaccagacuggcccucugcuagguuucg
guacgguggaaaaccguaccccuauccacaguacca
aaaggcaccaauggaacuggucauuaccuccuccga
aagucucgagugggaaaguuucgcgccugcugcuac
c.

In one preferred embodiment, the set of amplification oligonucleotides includes at least one detection probe, preferably one of the above-described detection probes, which preferentially hybridizes to the target sequence and not to nucleic acid derived from non-*T. vaginalis* organisms present in a test sample under stringent hybridization conditions. In another preferred embodiment, the set of oligonucleotides includes at least three oligonucleotides, preferably including one of the above-described detection probes and a pair of amplification oligonucleotides capable of amplifying all or a portion of the target sequence under amplification conditions, preferably including at least one of the above-described amplification oligonucleotides. And, in a particularly preferred embodiment, each member of the set of oligonucleotides contains an a target binding region which is fully complementary to a sequence contained within the target sequence, and none of the oligonucleotides includes any other base sequences which stably hybridize to nucleic acid derived from *T. vaginalis* under assay conditions.

The present invention further features methods for determining whether *T. vaginalis* is present in a test sample. In certain embodiments, the invention provides methods for determining whether *T. vaginalis* is present in a test sample, where such methods comprise the steps of: (a) contacting the test sample with one of the above-described detection probes for detecting *T. vaginalis* under conditions permitting the probe to preferentially hybridize to a target nucleic acid derived from *T. vaginalis*, thereby forming a probe:target hybrid stable for detection; and (b) determining whether the hybrid is present in the test sample as an indication of the presence or absence of *T. vaginalis* in the test sample. This method may further include the step of quantifying the amount of hybrid present in the test sample as a means for estimating the amount of *T. vaginalis* present in the test sample.

The methods for determining whether *T. vaginalis* is present in a test sample, or the amount of *T. vaginalis* present in a test sample, may further include the step of contacting the test sample with one of the above-described helper probes for facilitating hybridization of the detection probe to a target sequence and/or one of the above-described capture probes for isolating and purifying a target nucleic acid and/or one of the above-described amplification oligonucleotides appropriate for amplifying a target region present in nucleic acid derived from *T. vaginalis*, as desired.

The invention also contemplates methods for amplifying a target sequence contained in nucleic acid derived from *T. vaginalis* present in a test sample, where the method comprises the steps of: (a) contacting the test sample with at least one of the above-described amplification oligonucleotides; and (b) exposing the test sample to conditions sufficient to amplify the target sequence. Preferred amplification methods will include a set of at least two of the above-described amplification oligonucleotides.

In preferred embodiments, the methods for amplifying a target nucleic acid sequence present in nucleic acid derived from *T. vaginalis* will further include the steps of: (a) contacting the test sample with a detection probe which preferentially hybridizes to the target sequence or its complement under stringent hybridization conditions, thereby forming a probe:target hybrid stable for detection; and (b) determining whether the hybrid is present in the test sample as an indication of the presence or absence of *T. vaginalis* in the test sample. The above-described detection probes are preferred for these methods.

The invention also contemplates kits for determining whether *T. vaginalis* is present in a test sample. These kits include at least one of the above-described detection probes specific for a target sequence derived from *T. vaginalis* and optionally include written instructions for determining the presence or amount of *T. vaginalis* in a test sample. In another embodiment, the kits further include the above-described helper probe for aiding hybridization of the detection probe to the target sequence. In a further embodiment, the kits also include at least one of the above-described amplification oligonucleotides appropriate for amplifying the target sequence or its complement. In yet another embodiment, the kits further include the above-described capture probe for separating the target sequence from other components of the test sample prior to amplifying or directly detecting the target sequence or its complement. In still another embodiment, the kits additionally include at least two members of a group made up of one or more of the above-described amplification oligonucleotides, the above-described capture probe and the above-described helper probe.

The invention also contemplates kits for amplifying a target sequence present in nucleic acid derived from *T. vaginalis* which include at least one of the above-described amplification oligonucleotides and optionally include written instructions for amplifying nucleic acid derived from *T. vaginalis*. In another embodiment, the kits further include the above-described capture probe for separating the target sequence from other components of the test sample prior to amplifying the target sequence.

Those skilled in the art will appreciate that the detection probes of the present invention may be used as amplification oligonucleotides or capture probes, the amplification oligonucleotides of the present invention may be used as helper probes or capture probes, and the helper probes of the present invention may be used as amplification oligonucleotides or capture probes, depending upon the degree of specificity required.

Other features and advantages of the invention will be apparent from the following description of the preferred embodiments thereof and from the claims.

DESCRIPTION OF THE PREFERRED EMBODIMENTS

The present invention describes oligonucleotides targeted to nucleic acids derived from *T. vaginalis* which are particularly useful for determining the presence or absence of *T. vaginalis* in a test sample. The oligonucleotides can aid in detecting *T. vaginalis* in different ways, such as by functioning as detection probes, helper probes, capture probes and/or amplification oligonucleotides. Detection probes of the present invention can preferentially hybridize to a target nucleic acid sequence present in a target nucleic acid derived from *T. vaginalis* under stringent hybridization conditions to form detectable duplexes which indicate the presence of *T. vaginalis* in a test sample. Probes of the present invention are believed to be capable of distinguishing between *T. vaginalis* and its known closest phylogenetic neighbor. Helper probes of the present invention can hybridize to a target nucleic acid sequence present in nucleic acid derived from *T. vaginalis* under stringent hybridization conditions and can be used to enhance the formation of detection probe:target nucleic acid duplexes. Capture probes of the present invention can hybridize to a target nucleic acid sequence present in nucleic acid derived from *T. vaginalis* under assay conditions and can be used to separate target nucleic acid from other components of a clinical specimen. Amplification oligonucleotides of the present invention can hybridize to a target nucleic acid sequence present in nucleic acid derived from *T. vaginalis* under amplification conditions and can be used, for example, as primers in amplification reactions to generate multiple copies of *T. vaginalis*-derived nucleic acid. The probes and amplification oligonucleotides can be used in assays for the detection and/or quantitation of *T. vaginalis* in a test sample.

A. Definitions

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a genitourinary tract specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In the claims, the terms "sample" and "test sample" may refer to specimen in its raw form or to any stage of processing to release, isolate and purify nucleic acid derived from target organisms in the specimen. Thus, within a method of use claim, each reference to a "sample" or "test sample" may refer to a substance suspected of containing nucleic acid derived from the target organism or organisms at different stages of processing and is not limited to the initial form of the substance in the claim.

By "target nucleic acid" or "target" is meant a nucleic acid containing a target nucleic acid sequence.

By "target nucleic acid sequence," "target sequence" or "target region" is meant a specific deoxyribonucleotide or ribonucleotide sequence comprising all or part of the nucleotide sequence of a single-stranded nucleic acid molecule.

By "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. (Oligonucleotides including nucleoside subunits having 2' substitutions and which are useful as detection probes, helper probes, capture probes and/or amplification oligonucleotides are disclosed by Becker et al., "Method for Amplifying Target Nucleic Acids Using Modified Primers," U.S. Pat. No. 6,130,038.) The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are commonly referred to as "peptide nucleic acids" or "PNA", and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present invention, provided that the modified oligonucleotide can hybridize to a target nucleic acid under stringent hybridization conditions or amplification conditions. In the case of detection probes, the modified oligonucleotides must also be capable of preferentially hybridizing to the target nucleic acid under stringent hybridization conditions.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a detection probe. Oligonucleotides may also be used as helper probes, capture probes and amplification oligonucleotides.

By "detection probe" or "probe" is meant a structure comprising an oligonucleotide having a base sequence sufficiently complementary to its target nucleic acid sequence to form a probe:target hybrid stable for detection under stringent hybridization conditions. As would be understood by someone having ordinary skill in the art, the oligonucleotide is an isolated nucleic acid molecule, or an analog thereof, in a form not found in nature without human intervention (e.g., recombined with foreign nucleic acid, isolated, or purified to some extent). The probes of this invention may have additional nucleosides or nucleobases complementary to nucleotides outside of the targeted region so long as such nucleosides or nucleobases do not prevent hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "substantially homologous," "substantially corresponding," or "substantially corresponds" is meant that the subject oligonucleotide has a base sequence containing an at least 10 contiguous base region that is at least 80% homologous, preferably at least 90% homologous, and most preferably 100% homologous to an at least 10 contiguous base region present in a reference base sequence (excluding RNA and DNA equivalents). (Those skilled in the art will readily appreciate modifications that could be made to the hybridization assay conditions at various percentages of homology to permit hybridization of the oligonucleotide to the target sequence while preventing unacceptable levels of non-specific hybridization.) The degree of similarity is determined by comparing the order of nucleobases making up the two sequences and does not take into consideration other structural differences that may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "substantially complementary" is meant that the subject oligonucleotide has a base sequence containing an at least 10 contiguous base region that is at least 80% complementary, preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0 to 2 base mismatches.

By "about" is meant the nearest rounded whole number when referring to a percentage of complementarity or homology (e.g., a lower limit of 24.4 bases would be 24 bases and a lower limit of 24.5 bases would be 25 bases).

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" or "hybridize" is meant the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS (11th ed. 1992).)

By "preferentially hybridize" is meant that under stringent hybridization conditions, detection probes can hybridize to their target nucleic acids to form stable probe:target hybrids indicating the presence of at least one organism of interest, and there is not formed a sufficient number of stable probe: non-target hybrids to indicate the presence of non-targeted organisms, especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from *T. vaginalis*, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Preferably, there is at least a 10-fold difference between target and non-target hybridization signals in a test sample, more preferably at least a 100-fold difference, and most preferably at least a 1,000-fold difference. Preferably, non-target hybridization signals in a test sample are no more than the background signal level.

By "stringent hybridization conditions," or "stringent conditions" is meant conditions permitting a detection probe to preferentially hybridize to a target nucleic acid (preferably rRNA or rDNA derived from *T. vaginalis*) and not to nucleic acid derived from a closely related non-target microorganism. Stringent hybridization conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. Preferred hybridization assay conditions for detecting target nucleic acids derived from *T. vaginalis* with the probes of the present invention correspond to a temperature of about 60° C. when the salt concentration is in the range of about 0.6-0.9 M. Specific hybridization assay conditions are set forth infra in the Examples section and in the section entitled "Detection Probes to *Trichomonas vaginalis* Ribosomal Nucleic Acid." Other acceptable stringent hybridization conditions could be easily ascertained by someone having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

By "consists essentially of" or "consisting essentially of," when used with reference to an oligonucleotide herein, is meant that the oligonucleotide has a base sequence substantially homologous to a specified base sequence and may have up to four additional bases and/or two bases deleted therefrom. Thus, these phrases contain both a sequence length limitation and a sequence variation limitation. Any additions or deletions are non-material variations of the specified base sequence which do not prevent the oligonucleotide from having its claimed property, such as being able to preferentially hybridize under stringent hybridization conditions to its target nucleic acid over non-target nucleic acids. The oligonucleotide may contain a base sequence substantially similar to a specified nucleic acid sequence without any additions or deletions. However, a probe or primer containing an oligonucleotide consisting essentially of (or which consists essentially of) a specified base sequence may include other nucleic acid molecules which do not participate in hybridization of the probe to the target nucleic acid and which do not affect such hybridization.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means that do not require a probe associated label. For instance, the detection method may include a probe-coated substrate that is optically active and sensitive to changes in mass at its surface. Mass changes result in different reflective and transmissive properties of the optically active substrate in response to light and serve to indicate the presence or amount of immobilized target nucleic acid. (This exemplary form of optical detection is disclosed by Nygren et al., "Devices and Methods for Optical Detection of Nucleic Acid Hybridization," U.S. Pat. No. 6,060,237.) Other means for detecting the formation of a nucleic acid duplex that do not require the use of a labeled probe include the use of binding agents, which include intercalating agents such as ethidium bromide. See, e.g., Higuchi, "Homogenous Methods for Nucleic Amplification and Detection," U.S. Pat. No. 5,994,056.

By "amplification oligonucleotide" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification oligonucleotide is designed to initiate RNA synthesis, the primer may contain a base sequence which is non-complementary to the target sequence but which is recognized by a RNA polymerase such as a T7, T3, or SP6 RNA polymerase. An amplification oligonucleotide may contain a 3' terminus that is modified to prevent or lessen the rate or amount of primer extension. (McDonough et al., "Methods of Amplifying Nucleic Acids Using Promoter-Containing Primer Sequences," U.S. Pat. No. 5,766,849, disclose primers and promoter-primers having modified or blocked 3'-ends.) While the amplification oligonucleotides of the present invention may be chemically synthesized or derived from a vector, they are not naturally occurring nucleic acid molecules.

By "nucleic acid amplification" or "target amplification" is meant increasing the number of nucleic acid molecules having at least one target nucleic acid sequence. Target amplification according to the present invention may be either linear or exponential, although exponential amplification is preferred.

By "amplification conditions" is meant conditions permitting nucleic acid amplification. Acceptable amplification conditions could be readily ascertained without the exercise of anything more than routine experimentation by someone having ordinary skill in the art depending on the particular method of amplification employed.

By "antisense," "opposite sense," or "negative sense" is meant a nucleic acid molecule perfectly complementary to a reference, or sense, nucleic acid molecule.

By "sense," "same-sense," or "positive sense" is meant a nucleic acid molecule perfectly homologous to a reference nucleic acid molecule.

By "amplicon" is meant a nucleic acid molecule generated in a nucleic acid amplification reaction and which is derived from a target nucleic acid. An amplicon contains a target nucleic acid sequence that may be of the same or opposite sense as the target nucleic acid.

By "derived" is meant that the referred to nucleic acid is obtained directly from an organism or is the product of a nucleic acid amplification. Thus, a nucleic acid that is "derived" from an organism may be, for example, an antisense RNA molecule which does not naturally exist in the organism.

By "capture probe" is meant an oligonucleotide that is capable of binding to a target nucleic acid (preferably in a region other than that targeted by a detection probe) and, either directly or indirectly, to a solid support, thereby providing means for immobilizing and isolating the target nucleic acid in a test sample. The capture probe includes a target binding region that hybridizes to the target nucleic acid. Although the capture probe may include a member of ligand-ligate binding pair (e.g., avidin-biotin linkage) for immobilizing the capture probe on a solid support, preferred capture probes include an immobilized probe binding region that hybridizes to an immobilized probe bound to a solid support. While the capture probe preferably hybridizes to both the target nucleic acid and the immobilized probe under stringent conditions, the target binding and the immobilized probe binding regions of the capture probe may be designed to bind to their target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe. The target binding and immobilized probe binding regions may be contained within the same oligonucleotide, directly adjoining each other or separated by one or more optionally modified nucleotides, or these regions may be joined to each other by means of a non-nucleotide linker.

By "target binding region" is meant that portion of an oligonucleotide which stably binds to a target sequence present in a target nucleic acid, a DNA or RNA equivalent of the target sequence or a complement of the target sequence under assay conditions. The assay conditions may be stringent hybridization conditions or amplification conditions.

By "immobilized probe binding region" is meant that portion of an oligonucleotide which hybridizes to an immobilized probe under assay conditions.

By "homopolymer tail" in the claims is meant a contiguous base sequence of at least 10 identical bases (e.g., 10 contiguous adenines or thymines).

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "purify" or "purifying" is meant that one or more components of the test sample are removed from one or more other components of the sample. Sample components to be purified may include viruses, nucleic acids or, in particular, target nucleic acids in a generally aqueous solution phase which may also include undesirable materials such as proteins, carbohydrates, lipids, non-target nucleic acid and/or labeled probes. Preferably, the purifying step removes at least about 70%, more preferably at least about 90% and, even more preferably, at least about 95% of the undesirable components present in the sample.

By "helper probe" or "helper oligonucleotide" is meant an oligonucleotide designed to hybridize to a target nucleic acid at a different locus than that of a detection probe, thereby either increasing the rate of hybridization of the probe to the target nucleic acid, increasing the melting temperature ($T_m$) of the probe:target hybrid, or both.

By "phylogenetically closely related" is meant that the organisms are closely related to each other in an evolutionary sense and therefore would be expected to have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

B. Hybridization Conditions and Probe Design

Hybridization reaction conditions, most importantly the temperature of hybridization and the concentration of salt in the hybridization solution, can be selected to allow the detection probes or, in some cases, amplification oligonucleotides of the present invention to preferentially hybridize to a *T. vaginalis*-derived target nucleic acid and not to other non-target nucleic acids suspected of being present in a test sample. At decreased salt concentrations and/or increased temperatures (conditions of increased stringency) the extent of nucleic acid hybridization decreases as hydrogen bonding between paired nucleobases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular detection probe or amplification oligonucleotide and those of the target and non-target nucleic acids on the other, one or more mismatches will not necessarily defeat the ability of an oligonucleotide contained in the probe or amplification oligonucleotide to hybridize to the target nucleic acid and not to non-target nucleic acids.

The detection probes of the present invention were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state) and the $T_m$ of a mismatched hybrid formed between the probe and ribosomal RNA (rRNA) or ribosomal DNA (rDNA) of the phylogenetically most closely-related organisms expected to be present in the test sample, but not sought to be detected. While the unlabeled amplification oligonucleotides, capture probes and helper probes need not have such an extremely high degree of specificity as the detection probe to be useful in the present invention, they are designed in a similar manner to preferentially hybridize to one or more target nucleic acids over other nucleic acids under specified amplification, assay or stringent hybridization conditions.

To facilitate the identification of nucleic acid sequences to be used in the design of probes, nucleotide sequences from different organisms were first aligned to maximize homology. The source organisms and the associated nucleotide sequences used for this comparison were obtained from the GenBank database and had the following accession numbers: *Trichomonas vaginalis* (Accession No. U17510), *Trimastix pyriformis* (Accession No. AF244903), *Dientamoeba fragilis* (Accession No. U37461), *Trichomonas gallinae* (Accession No. U86614), *Trichomonas tenax* (Accession Nos. D49495 and U37711), *Tetratrichomonas gallinarum* (Accession No. AF124608), *Kalotennes flavicollis* (Accession No. AF215856), *Trichomitus trypanoides* (Accession No. X79559), *Hodotermopsis sjoestedti* (Accession No. AB032234), *Pentatrichomonas hominis* (Accession No. AF124609), *Pseudotrypanosoma giganteum* (Accession No. AF052706), *Ditrichomonas honigbergi* (Accession No. U17505), *Monotrichomonas* species ATCC50693 (Accession No. AF072905), *Pseudotrichomonas keilini* (Accession No. U17511), *Monocercomonas* species ATCC 50210 (Accession No. U17507), *Tritrichomonas foetus* (Accession No. U17509) and *Entamoeba histolytica* (Accession No. X64142).

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the detection probes described herein were identified by noting variations in the homology of the aligned sequences.

The sequence evolution at each of the variable regions is mostly divergent. Because of the divergence, corresponding rRNA variable regions of more distant phylogenetic relatives of *T. vaginalis* show greater differences from *T. vaginalis* rRNA than do the rRNAs of phylogenetically closer relatives. Sufficient variation between *T. vaginalis* and other organisms was observed to identify preferred target sites and to design detection probes useful for distinguishing *T. vaginalis* over non-*T. vaginalis* organisms in a test sample, particularly *Trichomonas tenax*, the most closely related organism to *T. vaginalis*.

Merely identifying putatively unique potential target nucleotide sequences does not guarantee that a functionally species-specific detection probe may be made to hybridize to *T. vaginalis* rRNA or rDNA comprising that sequence. Various other factors will determine the suitability of a nucleic acid locus as a target site for genus-specific or species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by Hogan et al., "Nucleic Acid Probes for Detection and/or Quantitation of Non-Viral Organisms," U.S. Pat. No. 5,840,488; Hogan et al., "Nucleic Acid Probes to *Mycobacterium gordonae*," U.S. Pat. No. 5,216,143; and Kohne, "Method for Detection, Identification and Quantitation of Non-Viral Organisms," U.S. Pat. No. 4,851,330. The contents of each of the foregoing references is hereby incorporated by reference herein.

The desired temperature of hybridization and the hybridization solution composition (such as salt concentration, detergents, and other solutes) can also greatly affect the stability of double-stranded hybrids. Conditions such as ionic strength and the temperature at which a probe will be allowed to hybridize to a target must be taken into account in constructing a genus-specific or species-specific probe. The thermal stability of hybrid nucleic acids generally increases with the ionic strength of the reaction mixture. On the other hand, chemical reagents that disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize to their targets under conditions of high stringency. Under such conditions only single nucleic acid strands having a high degree of complementarity will hybridize to each other. Single nucleic acid strands without such a high degree of complementarity will not form hybrids. Accordingly, the stringency of the assay conditions determines the amount of complementarity that should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the detection probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:non-target hybrids. In designing probes, the differences in these $T_m$ values should be as large as possible (preferably 2-5° C. or more). Manipulation of the $T_m$ can be accomplished by changes to probe length and probe composition (e.g., GC content versus AT content).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. (See, e.g., J. SAMBROOK ET AL., MOLECULAR CLONING: A LABORATORY MANUAL, ch. 11 ($2^{nd}$ ed. 1989).)

A preferred method to determine $T_m$ measures hybridization using the well known Hybridization Protection Assay (HPA) disclosed by Arnold et al., "Homogenous Protection Assay," U.S. Pat. No. 5,283,174, the contents of which are hereby incorporated by reference herein. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100 detergent, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® HC+ Luminometer (Gen-Probe Incorporated; San Diego, Calif.; Cat. No. 4747). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., Hogan et al., U.S. Pat. No. 5,840,488).

To ensure specificity of a detection probe for its target, it is preferable to design probes that hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra. Of course, alternative stringent hybridization conditions can be determined by those of ordinary skill in the art based on the present disclosure. (See, e.g., SAMBROOK ET AL., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another that differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions, especially in assays where helper probes described infra are not used. Likewise, probes with extensive self-complementarity are generally to be avoided, with specific exceptions being discussed below. If a strand is wholly or partially involved in an intramolecular or intermolecular hybrid, it will be less able to participate in the formation of a new intermolecular probe:target hybrid without a change in the reaction conditions. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does the product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.*, 98:503 (1975)).

A number of formulae are available which will provide an estimate of the melting temperature for perfectly matched oligonucleotides to their target nucleic acids. One such formula is the following:

$$T_m=81.5+16.6(\log_{10}[Na+])+0.41(\text{fraction } G+C)-(600/N)$$

(where N=the length of the oligonucleotide in number of nucleotides) provides a good estimate of the $T_m$ for oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference may be made to SAMBROOK ET AL., supra, ch. 11. This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification oligonucleotides of the present invention are oligodeoxynucleotides and are sufficiently long to be used as a substrate for the synthesis of extension products by a nucleic acid polymerase. Optimal amplification oligonucleotide length should take into account several factors, including the temperature of reaction, the structure and base composition of the amplification oligonucleotide, and how the amplification oligonucleotide is to be used. For example, for optimal specificity the oligonucleotide amplification oligonucleotide generally should be at least 12 bases in length, depending on the complexity of the target nucleic acid sequence. If such specificity is not essential, shorter amplification oligonucleotides may be used. In such a case, it may be desirable to carry out the reaction at cooler temperatures in order to form stable hybrid complexes with the template nucleic acid.

Useful guidelines for designing amplification oligonucleotides and detection probes with desired characteristics are described infra in the section entitled "Preparation of Oligonucleotides." Optimal sites for amplifying and probing contain at least two, and preferably three, conserved regions of *T. vaginalis* nucleic acid. These regions are about 15 to 350 bases in length, and preferably between about 15 and 150 bases in length.

The degree of amplification observed with a set of amplification oligonucleotides (e.g., primers and/or promoter-primers) depends on several factors, including the ability of the amplification oligonucleotides to hybridize to their specific target sequences and their ability to be extended or copied enzymatically. While amplification oligonucleotides of different lengths and base compositions may be used, amplification oligonucleotides preferred in this invention have target binding regions of 18 to 40 bases with a predicted $T_m$ to target of about 42° C.

Parameters affecting probe hybridization, such as $T_m$, complementarity, and secondary structure of the target sequence, also affect amplification oligonucleotide hybridization and therefore performance of the amplification oligonucleotides. The degree of non-specific extension (primer-dimer or non-target copying) can also affect amplification efficiency. Thus, amplification oligonucleotides are selected to have low self-complementarity or cross-complementarity, particularly at the 3' ends of their sequences. Notwithstanding, it should be noted that the "signal primers" described infra could be modified to include regions of self-complementarity, thereby transforming them into "molecular torch" or "molecular beacon" signal primers, such as these terms are defined below. Lengthy homopolymer runs and high GC content are avoided to reduce spurious primer extension. Computer programs are available to aid in this aspect of the design, including Oligo Tech analysis software which is available from Oligos Etc. Inc. and can be accessed on the World Wide Web at the following URL: http://www.oligosetc.com.

A nucleic acid polymerase used in conjunction with the amplification oligonucleotides of the present invention refers to a chemical, physical, or biological agent that incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilis* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. (In some applications, the amplification oligonucleotides may only consist of promoter-primers which are complementary to the sense strand, as disclosed by Kacian et al., "Nucleic Acid Sequence Amplification Method, Composition and Kit," U.S. Pat. No. 5,554,516.) A promoter-primer usually contains an oligonucleotide that is not complementary to a nucleotide sequence present in the target nucleic acid molecule or primer extension product(s) (see Kacian et al., "Nucleic Acid Sequence Amplification Methods," U.S. Pat. No. 5,399,491, for a description of such oligonucleotides). These non-complementary sequences may be located 5' to the complementary sequences on the amplification oligonucleotide and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well, unless the context of the reference clearly indicates otherwise.

In some amplification systems (see, e.g., the amplification methods disclosed by Dattagupta et al., "Isothermal Strand Displacement Amplification," U.S. Pat. No. 6,087,133), the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the primers need not be modified at their 5' ends.

1. Preparation of Oligonucleotides

The detection probes, capture probes, helper probes and amplification oligonucleotides of the present invention can be readily prepared by methods known in the art. Preferably, the oligonucleotides are synthesized using solid phase methods. For example, Caruthers describes using standard phosphoramidite solid-phase chemistry to join nucleotides by phosphodiester linkages. See Caruthers et al., "Chemical Synthesis of Deoxynucleotides by the Phosphoramidite Method," *Methods Enzymol.,* 154:287 (1987). Automated solid-phase chemical synthesis using cyanoethyl phosphoramidite precursors has been described by Barone. See Barone et al., "In Situ Activation of bis-dialkylaminephosphines—a New Method for Synthesizing Deoxyoligonucleotides on Polymer Supports," *Nucleic Acids Res.,* 12(10):4051 (1984). Likewise, Batt, "Method and Reagent for Sulfurization of Organophosphorous Compounds," U.S. Pat. No. 5,449,769, discloses a procedure for synthesizing oligonucleotides containing phosphorothioate linkages. In addition, Riley et al., "Process for the Purification of Oligomers,"U.S. Pat. No. 5,811,538 disclose the synthesis of oligonucleotides having different linkages, including methylphosphonate linkages. Moreover, methods for the organic synthesis of oligonucleotides are known to those of skill in the art and are described in, for example, SAMBROOK ET AL., supra, ch. 10.

Following synthesis of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether detection probes, helper probes, capture probes or amplification oligonucleotides, may be modified with chemical groups to enhance their performance or to facilitate the characterization of amplification products.

For example, backbone-modified oligonucleotides such as those having phosphorothioate, methylphosphonate, 2'-O-alkyl, or peptide groups which render the oligonucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a probe or primer, and which do not prevent hybridization of a probe or hybridization and elongation of a primer. (See Arnold et al., "Non-Nucleotide Linking Reagents for Nucleotide Probes," U.S. Pat. No. 6,031,091, the contents of which are hereby incorporated by reference herein.) The oligonucleotides of the present invention may also contain mixtures of the desired modified and natural nucleotides.

The 3' end of an amplification oligonucleotide, particularly a promoter-primer, may be modified or blocked to prevent or inhibit initiation of DNA synthesis, as disclosed by Kacian et al., U.S. Pat. No. 5,554,516. The 3' end of the primer can be modified in a variety of ways well known in the art. By way of example, appropriate modifications to a promoter-primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkane-diol modifications (see Wilk et al., "Backbone-Modified Oligonucleotides Containing a Butanediol-1,3 Moiety as a 'Vicarious Segment' for the Deoxyribosyl Moiety—Synthesis and Enzyme Studies," *Nucleic Acids Res.,* 18(8):2065 (1990)), or the modification may simply consist of a region 3' to the priming sequence that is non-complementary to the target nucleic acid sequence. Additionally, a mixture of different 3' blocked promoter-primers or of 3' blocked and unblocked promoter-primers may increase the efficiency of nucleic acid amplification, as described therein.

As disclosed above, the 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al., U.S. Pat. No. 6,031,091.

Once synthesized, a selected oligonucleotide may be labeled by any well known method (see, e.g., SAMBROOK ET AL., supra, ch. 10). Useful labels include radioisotopes as well as non-radioactive reporting groups. Isotopic labels include $^3$H, $^{35}$S, $^{32}$P, $^{125}$I, $^{57}$Co, and $^{14}$C. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as disclosed by Arnold et al., U.S. Pat. No. 6,031,091. Non-isotopic labels include fluorescent molecules (individual labels or combinations of labels, such as the fluorescence resonance energy transfer (FRET) pairs disclosed by Tyagi et al., "Detectably Labeled Dual Conformation Oligonucleotide Probes," U.S. Pat. No. 5,925,517), chemiluminescent molecules, enzymes, cofactors, enzyme substrates, haptens, or other ligands.

With the detection probes of the present invention, the probes are preferably labeled using of a non-nucleotide linker with an acridinium ester. Acridinium ester labeling may be performed as disclosed by Arnold et al., "Acridinium Ester Labelling and Purification of Nucleotide Probes," U.S. Pat. No. 5,185,439, the contents of which are hereby incorporated by reference herein.

2. Amplification of *Trichomonas vaginalis* Ribosomal Nucleic Acid

The amplification oligonucleotides of the present invention are directed to 18S regions of ribosomal nucleic acid derived from *T. vaginalis*. These amplification oligonucleotides may flank, overlap, or be contained within at least one of the target sequences of a detection probe (or its complement) used to detect the presence of *T. vaginalis* in a nucleic acid amplification assay. As indicated above, the amplification oligonucleotides may also include non-complementary bases at their 5' ends comprising a promoter sequence able to bind a RNA polymerase and direct RNA transcription using the target nucleic acid as a template. A T7 promoter sequence, such as SEQ ID NO:89, may be used.

Amplification oligonucleotides of the present invention are capable of amplifying a target region of nucleic acid derived from *T. vaginalis* under amplification conditions. The amplification oligonucleotides have a target binding region up to 40 bases in length which stably hybridizes to a target sequence selected from the group consisting of SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:57, SEQ ID NO:58, SEQ ID NO:59, SEQ ID NO:60, SEQ ID NO:61, SEQ ID NO:62, SEQ ID NO:63 and SEQ ID NO:64 under amplification conditions. The amplification oligonucleotide does not include any other base sequences which stably hybridize to nucleic acid derived from *T. vaginalis* under amplification conditions. Preferably, the base sequence of the target binding region comprises, overlaps with, consists essentially of, consists of, substantially corresponds to, or is contained within a base sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 and SEQ ID NO:88.

Alternatively, amplification oligonucleotides of the present invention consist of a target binding region up to 40 bases in length and an optional 5' sequence which is recognized by a RNA polymerase or which enhances initiation or elongation by a RNA polymerase, where the amplification oligonucleotide will, when contacted with a nucleic acid polymerase under amplification conditions, bind to or cause extension through a nucleic acid region having a base sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 or SEQ ID NO:88.

In one preferred embodiment, a set of at least two amplification oligonucleotides for amplifying *T. vaginalis*-derived nucleic acid is provided which includes: (i) a first amplification oligonucleotide having a target binding region up to 40 bases in length which stably hybridizes to a target sequence selected from the group consisting of SEQ ID NO:33, SEQ ID NO:34, SEQ ID NO:35 and SEQ ID NO:36 under amplification conditions; and (ii) a second amplification oligonucleotide having a target binding region up to 40 bases in length which stably hybridizes to a target sequence selected from the group consisting of SEQ ID NO:37, SEQ ID NO:38, SEQ ID NO:39 and SEQ ID NO:40 under amplification conditions. Preferably, the first amplification oligonucleotide has a target binding region which includes a base sequence comprising, overlapping with, consisting essentially of, consisting of, substantially corresponding to, or contained within a base sequence selected from the group consisting of SEQ ID NO:41, SEQ ID NO:42, SEQ ID NO:43, SEQ ID NO:44, SEQ ID NO:45, SEQ ID NO:46, SEQ ID NO:47 and SEQ ID NO:48, and the second amplification oligonucleotide has a target binding region which includes a base sequence comprising, overlapping with, consisting essentially of, consisting of, substantially corresponding to, or contained within a base sequence selected from the group consisting of SEQ ID NO:49, SEQ ID NO:50, SEQ ID NO:51, SEQ ID NO:52, SEQ ID NO:53, SEQ ID NO:54 SEQ ID NO:55 and SEQ ID NO:56. More preferably, the base sequence of the target binding region of the first amplification oligonucleotide comprises, overlaps with, consists essentially of, consists of, substantially corresponds to, or is contained within the base sequence of SEQ ID NO:41 or SEQ ID NO:45, and the base sequence of the target binding region of the second amplification oligonucleotide comprises, overlaps with, consists essentially of, consists of, substantially corresponds to, or is contained within the base sequence of SEQ ID NO:51 or SEQ ID NO:55. The second amplification oligonucleotide preferably includes a 5' promoter sequence (e.g., the T7 promoter sequence of SEQ ID NO:89).

In another preferred embodiment, a set of at least two amplification oligonucleotides for amplifying *T. vaginalis*-derived nucleic acid is provided which includes: (i) a first amplification oligonucleotide having a target binding region up to 40 bases in length which stably hybridizes to a target sequence selected from the group consisting of SEQ ID NO:57, SEQ ID NO:58, SEQ ID NO:59 and SEQ ID NO:60 under amplification conditions; and (ii) a second amplification oligonucleotide having a target binding region up to 40 bases in length which stably hybridizes to a target sequence selected from the group consisting of SEQ ID NO:61, SEQ ID NO:62, SEQ ID NO:63 and SEQ ID NO:64 under amplification conditions. Preferably, first amplification oligonucleotide has a target binding region which includes a base sequence comprising, overlapping with, consisting essentially of, consisting of, substantially corresponding to, or contained within a base sequence selected from the group consisting of SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75 and SEQ ID NO:76, and the second amplification oligonucleotide has a target binding region which includes a base sequence comprising, overlapping with, consisting essentially of, consisting of, substantially corresponding to, or contained within a base sequence of selected from the group consisting of SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 and SEQ ID NO:88. More preferably, the base sequence of the target binding region of the first amplification oligonucleotide comprises, overlaps with, consists essentially of, consists of, substantially corresponds to, or is contained within the base sequence of SEQ ID NO:65, SEQ ID NO:69 or SEQ ID NO:73, and base sequence of the target binding region of the second amplification oligonucleotide comprises, overlaps with, consists essentially of, consists of, substantially corresponds to, or is contained within the base sequence of SEQ ID NO:79, SEQ ID NO:83 or SEQ ID NO:87. The second amplification oligonucleotide preferably includes a 5' promoter sequence (e.g., the T7 promoter sequence of SEQ ID NO:89).

Amplification oligonucleotides of the present invention may have modifications, such as blocked 3' and/or 5' termini (as discussed above) or sequence additions including, but not limited to, a specific nucleotide sequence recognized by a RNA polymerase (e.g., a promoter sequence for T7, T3 or SP6 RNA polymerase), a sequence which enhances initiation or elongation of RNA transcription by a RNA polymerase, or a sequence which may provide for intra-molecular base pairing and encourage the formation of secondary or tertiary nucleic acid structures.

Amplification oligonucleotides are used in any suitable nucleic acid amplification procedure now known or later developed. Existing amplification procedures include the polymerase chain reaction (PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.*, 20:1691-1696 (1992); Fahy et al., "Self-sustained Sequence Replication (3SR): An Isothermal Transcription-Based Amplification System Alternative to PCR," *PCR Methods and Applications*, 1:25-33 (1991); Kacian et al., U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," European Patent Application No. 1 020 534 A1; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997). (Each of the foregoing amplification references is hereby incorporated by reference herein.) Any other amplification procedure which meets the definition of "nucleic acid amplification" supra is also contemplated by the inventors.

Amplification oligonucleotides of the present invention are preferably unlabeled but may include one or more reporter groups to facilitate detection of a target nucleic acid in combination with or exclusive of a detection probe. A wide variety of methods are available to detect an amplified target sequence. For example, the nucleotide substrates or the amplification oligonucleotides can include a detectable label that is incorporated into newly synthesized DNA. The resulting labeled amplification product is then generally separated from the unused labeled nucleotides or amplification oligonucleotides and the label is detected in the separated product fraction. (See, e.g., Wu, "Detection of Amplified Nucleic Acid Using Secondary Capture Oligonucleotides and Test Kit," U.S. Pat. No. 5,387,510.)

A separation step is not required, however, if the amplification oligonucleotide is modified by, for example, linking it to an interacting label pair, such as two dyes which form a donor/acceptor dye pair. The modified amplification oligonucleotide can be designed so that the fluorescence of one dye pair member remains quenched by the other dye pair member, so long as the amplification oligonucleotide does not hybridize to target nucleic acid, thereby physically separating the two dyes. Moreover, the amplification oligonucleotide can be further modified to include a restriction endonuclease recognition site positioned between the two dyes so that when a hybrid is formed between the modified amplification oligonucleotide and target nucleic acid, the restriction endonuclease recognition site is rendered double-stranded and available for cleavage or nicking by an appropriate restriction endonuclease. Cleavage or nicking of the hybrid then separates the two dyes, resulting in a change in fluorescence due to decreased quenching which can be detected as an indication of the presence of the target organism in the test sample. This type of modified amplification oligonucleotide, referred to as a "signal primer," is disclosed by Nadeau et al., "Detection of Nucleic Acids by Fluorescence Quenching," U.S. Pat. No. 6,054,279.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled oligonucleotide probe and measuring the resulting hybrids in any conventional manner. In particular, the product can be assayed by hybridizing a chemiluminescent acridinium ester-labeled oligonucleotide probe to the target sequence, selectively hydrolyzing the acridinium ester present on unhybridized probe, and measuring the chemiluminescence produced from the remaining acridinium ester in a luminometer. (See, e.g., Arnold et al., U.S. Pat. No. 5,283,174, and NORMAN C. NELSON ET AL., NONISOTOPIC PROBING, BLOTTING, AND SEQUENCING, ch. 17 (Larry J. Kricka ed., $2^{nd}$ ed. 1995).)

Because genitourinary specimens tend to contain large amounts of *T. vaginalis* when an individual is infected with the organism, it may be desirable to include a co-amplifiable pseudo target in the amplification reaction mixture in order to render the assay less sensitive, especially when quantification is an objective of the assay. Pseudo targets and their uses are disclosed by Nunomura, "Polynucleotide Amplification Method," U.S. Pat. No. 6,294,338, the contents of which are hereby included by reference herein. In the present application, the pseudo target may be, for example, a known amount of a *Trichomonas tenax* 18S rRNA transcript that can be amplified with a set of amplification oligonucleotides of the present invention under amplification conditions, but which does not contain or result in a sequence that is detectable with a detection probe of the present invention.

D. Sample Processing

Sample processing prior to amplification or detection of a target sequence may be necessary or useful for discriminating a target sequence from non-target nucleic acid present in a sample. Sample processing procedures may include, for example, direct or indirect immobilization of nucleic acids and/or oligonucleotides from the liquid phase in a heterogeneous assay. With some procedures, such immobilization may require multiple hybridization events. Ranki et al., "Detection of Microbial Nucleic Acids by a One-Step Sandwich Hybridization Test," U.S. Pat. Nos. 4,486,539 and 4,563,419, for example, disclose a one-step nucleic acid "sandwich" hybridization method involving the use of a solid-phase bound nucleic acid having a target complementary sequence and a labeled nucleic acid probe which is complementary to a distinct region of the target nucleic acid. Stabinsky, "Methods and Kits for Performing Nucleic Acid Hybridization Assays," U.S. Pat. No. 4,751,177, discloses methods including a "mediator" polynucleotide that reportedly overcomes sensitivity problems associated with Ranki's method resulting from leakage of immobilized probe from the solid support. Instead of directly immobilizing the target nucleic acid, the mediator polynucleotides of Stabinsky are used to bind and indirectly immobilize target polynucleotide:probe polynucleotide complexes which have formed free in solution.

Any known solid support may be used for sample processing, such as matrices and particles free in solution. The solid support may be, for example, nitrocellulose, nylon, glass, polyacrylate, mixed polymers, polystyrene, silane polypropylene and, preferably, particles having a magnetic charge to facilitate recovering sample and/or removing unbound nucleic acids or other sample components. Particularly preferred supports are magnetic spheres that are monodisperse (i.e., uniform in size ±5%), thereby providing consistent results, which is particularly advantageous for use in an automated procedure. One such automated procedure is disclosed by Ammann et al., "Automated Process for Isolating and Amplifying a Target Nucleic Acid Sequence," U.S. Pat. No. 6,335,166.

An oligonucleotide for immobilizing a target nucleic acid on a solid support may be joined directly or indirectly to the solid support by any linkage or interaction which is stable under assay conditions (e.g., conditions for amplification and/or detection). Referred to herein as an "immobilized probe," this oligonucleotide may bind directly to the target nucleic acid or it may include a base sequence region, such as a homopolymeric tract (e.g., a poly dT) or a simple short repeating sequence (e.g., an AT repeat), which hybridizes to a complementary base sequence region present on a capture probe. Direct joining occurs when the immobilized probe is joined to the solid support in the absence of an intermediate group. For example, direct joining may be via a covalent linkage, chelation or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary oligonucleotides, and complementary homopolymeric nucleic acids or homopolymeric portions of polymeric nucleic acids. Components of a binding partner set are the regions of the members that participate in binding.

A preferred sample processing system having practical advantages in terms of its ease of use and rapidity comprises an immobilized probe containing a base sequence which is complementary to a base sequence of a capture probe, referred to herein as an "immobilized probe binding region." The capture probe additionally contains a base sequence, referred to herein as a "target binding. region," which may specifically hybridize to a target sequence contained in a target nucleic acid under assay conditions. (While specificity of the target binding region of the capture probe for a region of the target nucleic acid is desirable to minimize the number of non-target nucleic acids remaining from the sample after a separation step, it is not a requirement of the capture probes of the present invention if the capture probes are being used solely to isolate target nucleic acid.) If the capture probe is not being employed to isolate a target nucleic acid for subsequent amplification of a target sequence, the capture probe may further include a detectable label attached within or near the target binding region, such as a substituted or unsubstituted acridinium ester. The labeled capture probe may be used in a homogeneous or semi-homogenous assay to specifically detect hybrid nucleic acids without detecting single-stranded nucleic acids, such as the capture probe. A preferred homogenous assay which could be used with this system is the hybridization protection assay (HPA), which is discussed above in the section entitled "Hybridization Conditions and Probe Design." Following the HPA format, label associated with capture probes which have not hybridized to target nucleic acids would be hydrolyzed with the addition of a mild base, while label associated with capture probe:target hybrids would be protected from hydrolysis.

An advantage of this latter assay system is that only a single target-specific hybridization event (capture probe: target) is necessary for target detection, rather than multiple such events (e.g., capture probe:target and probe:target or probe:amplicon) which are required in other sample processing procedures described herein. Also, fewer oligonucleotides in an assay tend to make the assay faster and simpler to optimize, since the overall rate at which a target nucleic acid is captured and detected is limited by the slowest hybridizing oligonucleotide. While the target binding region of a capture probe may be less specific in alternative assay systems, it must still be rare enough to avoid significant saturation of the capture probe with non-target nucleic acids. Thus, the requirement that two separate and specific target sequences be identified in these alternative systems could place constraints on the identification of an appropriate target. By contrast, only one such target sequence is needed when the capture probe simultaneously functions as the detection probe.

Whichever approach is adopted, the assay needs to include means for detecting the presence of the target nucleic acid in the test sample. A variety of means for detecting target nucleic acids are well known to those skilled in the art of nucleic acid detection, including means which do not require the presence of a detectable label. Nevertheless, probes including a detectable label are preferred. A labeled probe for detecting the presence of a target nucleic acid would have to include a base sequence which is substantially complementary and specifically hybridizes to a target sequence contained in the target nucleic acid. Once the probe stably binds to the target nucleic acid, and the resulting target:probe hybrid has been directly or indirectly immobilized, unbound probe can be washed away or inactivated and the remaining bound probe can be detected and/or measured.

Preferred sample processing systems combine the elements of detection and nucleic acid amplification. These systems first directly or indirectly immobilize a target nucleic acid using a capture probe, the captured target nucleic acid is purified by removing inter alia cellular debris, non-target nucleic acid and amplification inhibitors from the sample-containing vessel, which is followed by amplification of a target sequence contained in the target nucleic acid. Amplified product is then detected, preferably in solution with a labeled probe. (The target nucleic acid may remain in the immobilized state during amplification or it may be eluted from the solid support prior to amplification using appropriate conditions, such as by first incubating at a temperature above the $T_m$ of the capture probe:target complex and/or the $T_m$ of the capture probe:immobilized probe complex.) A preferred embodiment of this system is disclosed by Weisburg et al., "Two-Step Hybridization and Capture of a Polynucleotide," U.S. Pat. No. 6,110,678. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical samples) to prevent enzyme inhibition and/or nucleic acid degradation due to substances present in the sample.

A preferred amplification method is the transcription-mediated amplification method disclosed by Kacian et al., "Nucleic Acid Sequence Amplification Methods," U.S. Pat. No. 5,480,789. In accord with this method, a promoter-primer having a 3' region complementary to a portion of the target and a 5' promoter region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this preferred embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in the production of RNA amplicons of a sense opposite to that of the target nucleic acid. These amplicons can then be detected in solution by, for example, using an acridinium ester-labeled hybridization assay probe of the same sense as the target nucleic acid, employing HPA, as disclosed by Arnold et al. in U.S. Pat. No. 5,283,174.

The 3' terminus of the immobilized probe and the capture probe are preferably "capped" or blocked to prevent or inhibit their use as templates for nucleic acid polymerase activity. Capping may involve adding 3' deoxyribonucleotides (such as cordycepin), 3',2'-dideoxynucleotide residues, non-nucleotide linkers, such as those disclosed by Arnold et al. in U.S. Pat. No. 6,031,091, alkane-diol modifications, or non-complementary nucleotide residues at the 3' terminus.

Those skilled in the art will recognize that the above-described methodology is amenable, either as described or with obvious modifications, to various other amplification schemes, including, for example, the polymerase chain reaction (PCR), Qβ replicase-mediated amplification, self-sustained sequence replication (3SR), strand displacement amplification (SDA), nucleic acid sequence-based amplification (NASBA), loop-mediated isothermal amplification (LAMP), and the ligase chain reaction (LCR).

E. Capture Probes for Isolating *Trichomonas vaginalis* Ribosomal Nucleic Acid

Capture probes of the present invention are designed to bind to and isolate nucleic acid derived from the 18S ribosomal nucleic acid of *T. vaginalis* in the presence of non-target nucleic acid. As such, the capture probes preferably include both a target binding region and an immobilized probe binding region. The target binding region of the capture probes includes a base sequence which hybridizes to a target sequence derived from 18S ribosomal nucleic acid from *T. vaginalis* under assay conditions. While not essential, the target binding region preferably exhibits specificity for the target sequence in the presence of non-target nucleic acid under assay conditions. The immobilized probe binding region has a base sequence which hybridizes to an immobilized probe comprising a polynucleotide, or a chimeric containing polynucleotide sequences, which is joined to a solid support present in the test sample, either directly or indirectly. The target binding region and the immobilized probe binding region may be joined to each other directly or by means of, for example, a nucleotide base sequence, an abasic sequence or a non-nucleotide linker.

In a preferred embodiment, capture probes according to the present invention include a target binding region having a base sequence region which comprises, overlaps with, consists essentially of, consists of, substantially corresponds to, or is contained within the base sequence of SEQ ID NO:29, SEQ ID NO:30, SEQ ID NO:31 or SEQ ID NO:32. The immobilized probe binding region of these preferred capture probes comprises a base sequence which hybridizes to an immobilized probe joined directly or indirectly to a solid support provided to the test sample under assay conditions. Preferably, the immobilized probe binding region comprises a homopolymeric region (e.g., poly dA) located at the 3' end of the capture probe which is complementary to a homopolymeric region (e.g., poly dT) located at the 5' end of the immobilized probe. The immobilized probe binding region preferably consists of the base sequence of SEQ ID NO:98 tttaaaaaaaaaaaaaaaaaaaaaaaaaaaaaa. Other base sequences may be incorporated into the immobilized probe binding region, including, for example, short repeating sequences.

To prevent undesirable cross-hybridization reactions, the capture probes of the present invention preferably exclude nucleotide base sequences, other than the nucleotide base sequence of the target binding region, which can stably bind to nucleic acid derived from any organism which may be present in the test sample under assay conditions. Consistent with this approach, and in order to maximize the immobilization of capture probe:target complexes which are formed, the nucleotide base sequence of the immobilized probe binding region is preferably designed so that it can stably bind to a nucleotide base sequence present in the immobilized probe under assay conditions and not to nucleic acid derived from any organism which may be present in the test sample.

The target binding region and the immobilized probe binding region of the capture probe may be selected so that the capture probe:target complex has a higher $T_m$ than the $T_m$ of the capture probe:immobilized probe complex. In this way, a first set of conditions may be imposed which favors hybridization of the capture probe to the target sequence over the immobilized probe, thereby providing for optimal liquid phase hybridization kinetics for hybridization of the capture probe to the target sequence. Once sufficient time has passed for the capture probe to bind to the target sequence, a second set of less stringent conditions may be imposed which allows for hybridization of the capture probe to the immobilized probe.

Capture probes of the present invention may also include a label or a pair of interacting labels for direct detection of the target sequence in a test sample. Non-limiting examples of labels, combinations of labels and means for labeling probes are set forth supra in the section entitled "Preparation of Oligonucleotides" and infra in the section entitled "Detection Probes to *Trichomonas vaginalis* Ribosomal Nucleic Acid." A particularly useful method for detecting the presence of a capture probe hybridized to a target nucleic acid is the Hybridization Protection Assay (HPA), which is described above in the section entitled "Hybridization Conditions and Probe Design." HPA is a homogenous assay which distinguishes between probe hybridized to target nucleic acid and probe which remains unhybridized. Signal detected from an HPA reaction vessel provides an indication of the presence or amount of target organisms in the test sample.

Despite their application in a direct detection assay, the most common use of capture probes is in the isolation and purification of target nucleic acid prior to amplifying a target sequence contained in the target nucleic acid. By isolating and purifying the target nucleic acid prior to amplification, the number of unintended amplification reactions (i.e., amplification of non-target nucleic acid) can be severely limited. And, to prevent or inhibit the capture probe itself from functioning as a template for nucleic acid polymerase activity in the presence of amplification reagents and under amplification conditions, the 3' end of the capture probe may be capped or blocked. Examples of capping agents include 3' deoxyribonucleotides, 3',2'-dideoxynucleotide residues, non-nucleotide linkers, alkane-diol modifications, and non-complementary nucleotide residues at the 3' terminus.

F. Detection Probes to *Trichomonas vaginalis* Ribosomal Nucleic Acid

This embodiment of the invention relates to novel detection probes. Hybridization is the association of two single strands of complementary nucleic acid to form a hydrogen-bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA, as well as between single-stranded nucleic acids wherein one or both strands of the resulting hybrid contain at least one modified nucleotide, nucleoside, nucleobase, and/or base-to-base linkage. In any case, two single strands of sufficient complementarity may hybridize to form a double-stranded structure in which the two strands are held together by hydrogen bonds between pairs of complementary bases. As described above, in general A is hydrogen-bonded to T or U, while G is hydrogen-bonded to C. At any point along the hybridized strands, therefore, the classical base pairs AT or AU, TA or UA, GC, or CG may be found. Thus, when a first single strand of nucleic acid contains sufficient contiguous complementary bases to a second, and those two strands are brought together under conditions that promote their hybridization, double-stranded nucleic acid will result. Accordingly, under appropriate conditions, double-stranded nucleic acid hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a single-stranded probe and require denaturation (in at least the region to be targeted by the probe) prior to the hybridization step. In addition, there can be intra-molecular and inter-molecular hybrids formed within a probe if there is sufficient self-complementarity. Regions of the nucleic acid known or expected to form strong internal structures inhibitory to hybridization are less preferred. Examples of such structures include hairpin loops. Likewise, probes with extensive self-complementarity generally should be avoided. All these undesirable structures can be avoided through careful probe design, and commercial computer programs are available to search for these types of interactions, such as the Oligo Tech analysis software.

In some applications, probes exhibiting at least some degree of self-complementarity are desirable to facilitate detection of probe:target duplexes in a test sample without first requiring the removal of unhybridized probe prior to detection. Molecular torch probes are a type of self-complementary probes that are disclosed by Becker et al., "Molecular Torches," U.S. Pat. No. 6,361,945. The molecular torch probes disclosed Becker et al. have distinct regions of self-complementarity, referred to as "the target binding domain" and "the target closing domain," which are connected by a joining region and which hybridize to one another under predetermined hybridization assay conditions. When exposed to denaturing conditions, the complementary regions (which may be fully or partially complementary) of the molecular torch probe melt, leaving the target binding domain available for hybridization to a target sequence when the predetermined hybridization assay conditions are restored. And when exposed to strand displacement conditions, a portion of the target sequence binds to the target binding domain and displaces the target closing domain from the target binding domain. Molecular torch probes are designed so that the target binding domain favors hybridization to the target sequence over the target closing domain. The target binding domain and the target closing domain of a molecular torch probe include interacting labels (e.g., luminescent/quencher) positioned so that a different signal is produced when the molecular torch probe is self-hybridized as opposed to when the molecular torch probe is hybridized to a target nucleic acid, thereby permitting detection of probe:target duplexes in a test sample in the presence of unhybridized probe having a viable label or labels associated therewith.

Another example of detection probes having self-complementarity are the molecular beacon probes disclosed by Tyagi et al. in U.S. Pat. No. 5,925,517. Molecular beacon probes include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and quencher, such as DABCYL and EDANS.

The rate at which a probe hybridizes to its target is one measure of the thermal stability of the target secondary structure in the probe region. The standard measurement of hybridization rate is the $C_o t_{1/2}$, which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_o t_{1/2}$ is found graphically by standard procedures. The probe:target hybrid melting temperature may be determined by isotopic methods well-known to those skilled in the art. The melting temperature ($T_m$) for a given hybrid will vary depending on the hybridization solution being used.

Preferred detection probes are sufficiently complementary to the target nucleic acid sequence, or its complement, to hybridize therewith under stringent hybridization conditions corresponding to a temperature of about 60° C. when the salt concentration is in the range of about 0.6-0.9 M. Preferred salts include lithium chloride, but other salts such as sodium chloride and sodium citrate also can be used in the hybridization solution. Examples of high stringency hybridization conditions are alternatively provided by 0.48 M sodium phosphate buffer, 0.1% sodium dodecyl sulfate, and 1 mM each of EDTA and EGTA at a temperature of about 60° C., or by 0.6 M LiCl, 1% lithium lauryl sulfate (LLS), 60 mM lithium succinate and 10 mM each of EDTA and EGTA at a temperature of about 60° C.

Thus, in a first aspect, the present invention features detection probes able to distinguish *T. vaginalis*-derived nucleic acid from non-*T. vaginalis* nucleic acid (e.g., *Trichomonas tenax*) by virtue of the ability of the detection probe to preferentially hybridize to *T. vaginalis*-derived nucleic acid) under stringent hybridization conditions. Specifically, the detection probes contain an oligonucleotide having a base sequence that is substantially complementary to a target sequence present in *T. vaginalis*-derived nucleic acid.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability. While probes of different lengths and base composition may be used, the probes preferred in the present invention are up to 100 bases in length, more preferably from 12 to 50 bases in length, and even more preferably from 18 to 35 bases in length.

The detection probes include a base sequence that is substantially complementary to a target sequence present in 18S ribosomal RNA (rRNA), or the encoding DNA (rDNA), of *T. vaginalis*. Thus, the detection probes are able to stably hybridize to a target sequence derived from *T. vaginalis* under stringent hybridization conditions. The detection probes may also have additional bases outside of the targeted nucleic acid region which may or may not be complementary to *T. vaginalis*-derived nucleic acid but which are not complementary to nucleic acid derived from a non-target organism which may be present in the test sample.

Probes (and amplification oligonucleotides) of the present invention may also be designed to include a capture tail comprised of a base sequence (distinct from the base sequence intended to hybridize to the target sequence) that can hybridize under predetermined hybridization conditions to a substantially complementary base sequence present in an immobilized oligonucleotide that is joined to a solid support. The immobilized oligonucleotide is preferably joined to a magnetically charged particle that can be isolated in a reaction vessel during a purification step after a sufficient period of time has passed for probe to hybridize to target nucleic acid. (An example of an instrument which can be used to perform such a purification step is the DTS™ 1600 Target Capture System (Gen-Probe; Cat. No. 5202).) The probe is preferably designed so that the melting temperature of the probe:target hybrid is greater than the melting temperature of the probe:immobilized oligonucleotide hybrid. In this way, different sets of hybridization assay conditions can be employed to facilitate hybridization of the probe to the target nucleic acid prior to hybridization of the probe to the immobilized oligonucleotide, thereby maximizing the concentration of free probe and providing favorable liquid phase hybridization kinetics. This "two-step" target capture method is disclosed by Weisburg et al., "Two Step Hybridization and Capture of a Polynucleotide," U.S. Pat. No. 6,110,678, the contents of which are hereby incorporated by reference herein. Other target capture schemes which could be readily adapted to the present invention are well known in the art and include, for example, those disclosed by Ranki et al., "Detection of Microbial Nucleic Acids by a One-Step Sandwich Hybridization Test," U.S. Pat. No. 4,486,539, and Stabinsky, "Methods and Kits for Performing Nucleic Acid Hybridization Assays," U.S. Pat. No. 4,751,177.

For *T. vaginalis* detection probes, the terms "target nucleic acid sequence," "target nucleotide sequence," "target sequence," and "target region" all refer to a nucleic acid sequence present in *T. vaginalis* rRNA or rDNA, or a sequence complementary thereto, which is not identically present in the nucleic acid of a closely related species. Nucleic acids having nucleotide sequences complementary to a target sequence may be generated by target amplification techniques disclosed elsewhere herein.

Organisms closely related to *T. vaginalis* include *Trichomonas gallinae, Trichomonas tenax, Monotrichomonas* species ATCC 50693, *Ditrichomonas honigbergi, Tritrichomonas foetus, Tetratrichomonas gallinarum* and *Pentatrichomonas hominis*, with *Trichomonas tenax* being the most closely related. In addition to these organisms, organisms that might be expected to be present in a *T. vaginalis*-containing test sample include, for example, *Escherichia coli, Chlamydia trachomatis* and *Neiserria gonorrhoeae*. These lists of organisms are by no means intended to be fully representative of the organisms that the *T. vaginalis* detection probes of the present invention can be used to distinguish over. In general, the *T. vaginalis* detection probes of the present invention can be used to distinguish *T. vaginalis*-derived nucleic acid from any non-*T. vaginalis* nucleic acid that does not stably hybridize with the probe(s) under stringent hybridization conditions.

In one embodiment, *T. vaginalis* detection probes of the present invention are preferably up to 100 bases in length and comprise a target binding region which forms a hybrid stable for detection with a sequence contained within a target sequence selected from the group consisting of SEQ ID NO:1, SEQ ID NO:2, SEQ ID NO:3 and SEQ ID NO:4. More preferably, the base sequence of the target binding region comprises, overlaps with, consists essentially of, consists of, substantially corresponds to, or is contained within the base sequence of SEQ ID NO:1, SEQ ID NO:2, SEQ ID NO:3 or SEQ ID NO:4. In a particularly preferred mode, these detection probes include an acridinium ester label joined to the probes by means of a non-nucleotide linker positioned between nucleotides 17 and 18 (reading 5' to 3') of SEQ ID NO:1 or SEQ ID NO:2 and between nucleotides 15 and 16 (reading 5' to 3') of SEQ ID NO:3 or SEQ ID NO:4. The acridinium ester label may be joined to the probe in accordance with the teachings of Arnold et al. in U.S. Pat. Nos. 5,185,439 and 6,031,091.

In another embodiment of the present invention, *T. vaginalis* detection probes are preferably up to 100 bases in length and comprise a target binding region which forms a hybrid stable for detection with a sequence contained within a target sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14, SEQ ID NO:15 or SEQ ID NO:16. More preferably, the base sequence of the target binding region comprises, overlaps with, consists essentially of, consists of, substantially corresponds to, or is contained within the base sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14, SEQ ID NO:15 or SEQ ID NO:16. One group of preferred *T. vaginalis* detection probes has a target binding region comprising, overlapping with, consisting essentially of, consisting of, substantially corresponding to, or contained within the base sequence of SEQ ID NO:5, SEQ ID NO:6, SEQ ID NO:7 or SEQ ID NO:8, and which may include an acridinium ester label joined to the probe by means of a non-nucleotide linker positioned between, for example, nucleotides 12 and 13 (reading 5' to 3') of SEQ ID NO:5 or SEQ ID NO:6 and between, for example, nucleotides 18 and 19 (reading 5' to 3') of SEQ ID NO:7 or SEQ ID NO:8. Another group of preferred *T. vaginalis* detection probes has a target binding region comprising, overlapping with, consisting essentially of, consisting of, substantially corresponding to, or contained within the base sequence of SEQ ID NO:9, SEQ ID NO:10, SEQ ID NO:11 or SEQ ID NO:12, and which may include an acridinium ester label joined to the probe by means of a non-nucleotide linker positioned between, for example, nucleotides 17 and 18 (reading 5' to 3') of SEQ ID NO:9 or SEQ ID NO:10 and between, for example, nucleotides 9 and 10 (reading 5' to 3') of SEQ ID NO:11 or SEQ ID NO:12. A further group of preferred *T. vaginalis* probes has a target binding region comprising, overlapping with, consisting essentially of, consisting of, substantially corresponding to, or contained within the base sequence of SEQ ID NO:13, SEQ ID NO:14, SEQ ID NO:15 or SEQ ID NO:16, and which may include an acridinium ester label joined to the probe by means of a non-nucleotide linker positioned between, for example, nucleotides 8 and 9 (reading 5' to 3') of SEQ ID NO:13 or SEQ ID NO:14 and between, for example, nucleotides 19 and 20 (reading 5' to 3') of SEQ ID NO:15 or SEQ ID NO:16. The acridinium ester label may be joined to the probe in accordance with the teachings of Arnold et al. in U.S. Pat. Nos. 5,185,439 and 6,031,091.

Thus, in one aspect of the present invention a detection probe is provided which is useful for determining whether *T. vaginalis* is present in a test sample. The probe is up to 100 bases in length and comprises a target binding region having a base sequence which comprises, overlaps with, consists essentially of, consists of, substantially corresponds to, or is contained within a base sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16. The probe preferentially hybridizes under stringent hybridization conditions to a target nucleic acid derived from *T. vaginalis* over nucleic acid derived from non-*T. vaginalis* organisms present in the test sample. In particular, the probe does not form a hybrid stable for detection with *Trichomonas tenax* under the stringent hybridization conditions used.

Once synthesized, the probes may be labeled with a detectable label or reporter group by any well-known method. (See, e.g., SAMBROOK ET AL., supra, ch. 10.) The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^{3}H$, $^{35}S$, $^{32}P$, $^{125}I$, $^{57}Co$ and $^{14}C$. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al. in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably hybridize to the target nucleic acid under stringent conditions. Probes of the present invention are preferably labeled with an acridinium ester. (Acridinium ester labeling is disclosed by Arnold et al. in U.S. Pat. No. 5,185,439.)

The selected detection probe can then be brought into contact with a test sample suspected of containing *T. vaginalis*. Generally, the test sample is from a source that also contains unknown organisms. Typically, the source of the test sample will be a patient specimen, such as a genitourinary specimen. After bringing the probe into contact with nucleic acids derived from the test sample, the probe and sample-derived nucleic acids can be incubated under conditions permitting preferential hybridization of the probe to a target nucleic acid derived from *T. vaginalis* that may be present in the test sample in the presence of nucleic acid derived from other organisms present in the test sample.

Detection probes may also be combined with one or more unlabeled helper probes to facilitate binding to target nucleic acid derived from *T. vaginalis*. After a detection probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed in U.S. Pat. No. 5,283,174. The inventors particularly prefer this latter technique.

G. Helper Probes Used in the Detection of *Trichomonas vaginalis*

Another embodiment of this invention relates to novel helper probes. As mentioned above, helper probes can be used to facilitate hybridization of detection probes to their intended target nucleic acids, so that the detection probes more readily form probe:target nucleic acid duplexes than they would in the absence of helper probes. (Helper probes are disclosed by Hogan et al., "Means and Method for Enhancing Nucleic Acid Hybridization," U.S. Pat. No. 5,030,557.) Each helper probe contains an oligonucleotide that is sufficiently complementary to a target nucleic acid sequence to form a helper probe:target nucleic acid duplex under stringent hybridization conditions. The stringent hybridization conditions employed with a given helper probe are determined by the conditions used for preferentially hybridizing the associated detection probe to the target nucleic acid.

Regions of single-stranded RNA and DNA can be involved in secondary and tertiary structures even under stringent hybridization conditions. Such structures can sterically inhibit or block hybridization of a detection probe to a target nucleic acid. Hybridization of the helper probe to the target nucleic acid alters the secondary and tertiary structure of the target nucleic acid, thereby rendering the target region more accessible by the detection probe. As a result, helper probes enhance the kinetics and/or the melting temperature of the detection probe:target nucleic acid duplex. Helper probes are generally selected to hybridize to nucleic acid sequences located near the target region of the detection probe.

Helper probes which can be used with the *T. vaginalis* detection probes of the present invention are targeted to nucleic acid sequences within *T. vaginalis*-derived nucleic acid. Likewise, helper probes which can be used with the *T. vaginalis* detection probes of the present invention are targeted to nucleic acid sequences within *T. vaginalis*-derived nucleic acid. Each helper probe comprises an oligonucleotide which targets and stably hybridizes to a base region present in nucleic acid derived from *T. vaginalis* under stringent hybridization conditions. Helper probes and their associated detection probes have different target sequences contained within the same target nucleic acid. The helper probes of the present invention are preferably oligonucleotides up to 100 bases in length, more preferably from 12 to 50 bases in length, and even more preferably from 18 to 35 bases in length.

Preferred *T. vaginalis* helper probes useful in the present invention have a base sequence comprising, overlapping with, consisting essentially of, consisting of, substantially corresponding to, or contained within the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28. The preferred *T. vaginalis* detection probe for use with one or more of these helper probes has a target binding region comprising, overlapping with, consisting essentially of, consisting of, substantially corresponding to, or contained within the base sequence of SEQ ID NO:1, SEQ ID NO:2, SEQ ID NO:3 or SEQ ID NO:4, where the detection probe preferentially hybridizes under stringent hybridization conditions to a target nucleic acid derived from *T. vaginalis* over nucleic acid derived from non-*T. vaginalis* organisms present in a test sample. In particular, the probe does not form a hybrid stable for detection with *Trichomonas tenax* under the stringent hybridization conditions used.

H. Nucleic Acid Compositions

In another related aspect, the present invention features compositions comprising a nucleic acid hybrid formed between a detection probe and a target nucleic acid ("probe: target") under stringent hybridization conditions. One use of the hybrid formed between a probe and a target nucleic acid is to provide an indication of the presence or amount of a target organism or group of organisms in a test sample. For example, acridinium ester (AE) present in nucleic acid hybrids is resistant to hydrolysis in an alkali solution, whereas AE present in single-stranded nucleic acid is susceptible to hydrolysis in an alkali solution (see U.S. Pat. No. 5,238,174). Thus, the presence of target nucleic acids can be detected, after the hydrolysis of the unbound AE-labeled probe, by measuring chemiluminescence of acridinium ester remaining associated with the nucleic acid hybrid.

The present invention also contemplates compositions comprising nucleic acid hybrids formed between a capture probe and a target nucleic acid ("capture probe:target") under stringent hybridization conditions. One use of the hybrid formed between a capture probe and a target nucleic acid is to isolate and purify the target nucleic acid in a test sample prior to amplification of a target sequence contained in the target nucleic acid or detection of the target nucleic acid in, for example, a heterogenous assay. By isolating and purifying target nucleic acid prior to amplification or detection, the opportunities for non-specific binding or amplification are significantly minimized.

The present invention further contemplates compositions comprising nucleic acid hybrids formed between a helper probe and a target nucleic acid ("helper probe:target") under stringent hybridization conditions. One use of the hybrid formed between a helper probe and a target nucleic acid is to make available a particular nucleic acid sequence for hybridization. For example, a hybrid formed between a helper probe and a target nucleic acid may render a nucleic acid sequence available for hybridization with a hybridization assay probe. A full description of the use of helper probes is provided by Hogan et al. in U.S. Pat. No. 5,030,557.

The present invention also features compositions comprising a nucleic acid formed between an amplification oligonucleotide and a target nucleic acid ("amplification oligonucleotide:target") under amplification conditions. One use of the hybrid formed between a primer and a target nucleic acid is to provide an initiation site for a nucleic acid polymerase at the 3' end of the amplification oligonucleotide. For example, a hybrid may form an initiation site for reverse transcriptase, DNA polymerases such as Taq polymerase or T4 DNA polymerase, and RNA polymerases such as T7 polymerase, SP6 polymerase, T3 polymerase, and the like.

Compositions of the present invention include compositions for determining the presence or amount of T. vaginalis in a test sample comprising a nucleic acid hybrid formed between a target nucleic acid derived from T. vaginalis and one or more oligonucleotides, where the base sequence of each oligonucleotide comprises, overlaps with, consists essentially of, consists of, substantially corresponds to, or is contained within the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12,SEQ ID NO:13, SEQ ID NO:14,SEQ ID NO:15, SEQ ID NO:16,SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 or SEQ ID NO:88. The oligonucleotides of these compositions may include at least one additional nucleotide base sequence region which does not stably bind to nucleic acid derived from T. vaginalis under stringent hybridization conditions. In another embodiment, the probe:target compositions may further comprise at least one helper probe hybridized to the T. vaginalis-derived target nucleic acid.

The present invention also contemplates compositions for determining the presence or amount of T. vaginalis in a test sample comprising a nucleic acid hybrid formed between a target nucleic acid derived from T. vaginalis and a detection probe, where the base sequence of the detection probe comprises, overlaps with, consists essentially of, consists of, substantially corresponds to, or is contained within the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 or SEQ ID NO:16.

Also contemplated by the present invention are compositions for immobilizing a target nucleic acid derived from a T. vaginalis present in a test sample comprising a nucleic acid hybrid formed between the target nucleic acid and a capture probe comprising a target binding region which comprises, overlaps with, consists essentially of, consists of, substantially corresponds to, or is contained within the base sequence of SEQ ID NO:29, SEQ ID NO:30, SEQ ID NO:31 or SEQ ID NO:32. In a further embodiment, these compositions additionally include a nucleic acid hybrid formed between an immobilized probe binding region of the capture probe and an immobilized probe.

The present invention also contemplates compositions for amplifying a target sequence present in a target nucleic acid derived from T. vaginalis, where the compositions comprise a nucleic acid hybrid formed between the target nucleic acid and an amplification oligonucleotide, where the base sequence of the amplification oligonucleotide comprises, overlaps with, consists essentially of, consists of, substantially corresponds to, or consists of the base sequence of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 or SEQ ID NO:88. The amplification primer of these compositions optionally includes a 5' sequence which is recognized by a RNA polymerase or which enhances initiation or elongation by a RNA polymerase. When included, a T7 promoter, such as the nucleotide base sequence of SEQ ID NO:89, is preferred.

I. Assay Methods

The present invention contemplates various methods for assaying for the presence or amount of nucleic acid derived from *T. vaginalis* in a test sample. One skilled in the art will understand that the exact assay conditions, probes, and/or amplification oligonucleotides used will vary depending on the particular assay format used and the source of the sample.

One aspect of the present invention relates to a method for determining the presence or amount of *T. vaginalis* in a test sample by contacting the test sample under stringent hybridization conditions with a detection probe capable of preferentially hybridizing under stringent hybridization hybridization conditions to a *T. vaginalis*-derived target nucleic acid over nucleic acids from non-*T. vaginalis* organisms present in the test sample. In such methods, the target nucleic acid contains a base sequence having or substantially corresponding to the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 or SEQ ID NO:16. (Depending on the source, the test sample may contain unknown organisms that the probes of this method can distinguish over.) The base sequence of a preferred probe for use in this method comprises, overlaps with, consists essentially of, consists of, substantially corresponds to, or is contained within the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 or SEQ ID NO:16.

In one preferred embodiment, the method for determining the presence or amount of *T. vaginalis* in a test sample may also include the step of contacting the test sample with one or more helper probes for facilitating hybridization of the probe to the target nucleic acid. While the helper probes may be added to the sample before or after the addition of the detection probe, the helper probes and detection probe are preferably provided to the test sample at the same time. The base sequence of a preferred helper probe for use in this method comprises, overlaps with, consists essentially of, consists of, substantially corresponds to, or is contained within the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28, and is used in combination with a detection probe, where the base sequence of the detection probe comprises, overlaps with, consists essentially of, consists of, substantially corresponds to, or is contained within the base sequence of SEQ ID NO:1, SEQ ID NO:2, SEQ ID NO:3 or SEQ ID NO:4, and where the detection probe preferentially hybridizes to *T. vaginalis*-derived nucleic acid over nucleic acid derived from non-*T. vaginalis* organisms present in the test sample under stringent hybridization conditions.

Another aspect of the present invention relates to a method for amplifying *T. vaginalis*-derived nucleic acid in a test sample by contacting the test sample under amplification conditions with one or more amplification oligonucleotides which, when contacted with a nucleic acid polymerase, will bind to or cause elongation through a nucleic acid region having a base sequence of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 or SEQ ID NO:88. The amplification oligonucleotide optionally includes a nucleic acid sequence recognized by a RNA polymerase or which enhances initiation or elongation by a RNA polymerase. Particular combinations of amplification oligonucleotides that can be used in this method are set forth above under the heading "Amplification of *Trichomonas vaginalis* Ribosomal Nucleic Acid."

In preferred embodiments, the methods for amplifying *T. vaginalis*-derived nucleic acid in a test sample further include the step of contacting the test sample under stringent hybridization conditions with a detection probe capable of preferentially hybridizing under stringent hybridization conditions to an amplified *T. vaginalis* target nucleic acid over nucleic acids from non-*T. vaginalis* organisms present in the test sample. While the test sample is generally contacted with the detection probe after a sufficient period for amplification has passed, the amplification oligonucleotides and detection probe may be added to the sample in any order, as when the detection probe is a self-hybridizing probe, such as a molecular torch probe discussed supra. This step of contacting the test sample with a detection probe is performed so that the presence or amount of *T. vaginalis* in the test sample can be determined. The base sequence of a preferred probe for use in this method comprises, overlaps with, consists essentially of, consists of, substantially corresponds to, or is contained within the base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15 or SEQ ID NO:16. The detection probes may further include a label to facilitate detection in the test sample.

In certain preferred embodiments, these methods are carried out with a set of at least two amplification oligonucleotides for amplifying *T. vaginalis*-derived nucleic acid Preferred sets of amplification oligonucleotides that can be used in these methods are set forth above under the heading "Amplification of *Trichomonas vaginalis* Ribosomal Nucleic Acid."

Still another aspect of the present invention relates to a method for immobilizing a target nucleic acid derived from a *T. vaginalis* in a test sample which comprises providing to the test sample a capture probe having a target binding region and an immobilized probe binding region under a first set of hybridization conditions permitting the capture probe to stably bind the target nucleic acid, thereby forming a capture probe:target complex, and a second set of hybridization conditions permitting the capture probe to stably bind to an immobilized probe in the test sample, thereby forming an immobilized probe:capture probe:target complex. The first and second sets of hybridization conditions may be the same or different and the capture probe:target complex remains stable under the second set of hybridization conditions. The target binding region of this capture probe comprises, overlaps with, consists essentially of, consists of, substantially corresponds to, or consists of the base sequence of SEQ ID NO:29, SEQ ID NO:30, SEQ ID NO:31 or SEQ ID NO:32. A purifying step preferably follows the immobilizing step to remove one or more components of the test sample that might interfere with or prevent amplification or specific detection of a target sequence contained in the immobilized target nucleic acid. This method for immobilizing and optionally purifying a *T. vaginalis*-derived nucleic may precede any of the methods described above for amplifying and/or detecting the presence of a target nucleic acid derived from *T. vaginalis*. If a purifying step is included, the target nucleic acid may be indirectly eluted from the immobilized probe or directly eluted from the capture probe of the immobilized probe: capture probe:target complex by altering the sample conditions prior to amplifying or detecting the target sequence.

J. Diagnostic Systems

The present invention also contemplates diagnostic systems in kit form. A diagnostic system of the present invention may include a kit that contains, in an amount sufficient for at least one assay, any of the detection probes, helper probes, capture probes and/or amplification oligonucleotides of the present invention in a packaging material. Typically, the kits will also include instructions recorded in a tangible form (e.g., contained on paper or an electronic medium, such as a disk, CD-ROM, DVD or video tape) for using the packaged probes and/or amplification oligonucleotides in an amplification and/or detection assay for determining the presence or amount of *T. vaginalis* in a test sample.

The various components of the diagnostic systems may be provided in a variety of forms. For example, the required enzymes, the nucleotide triphosphates, the probes and/or primers may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit. In preferred kits for amplifying target nucleic acid derived from *T. vaginalis*, the enzymes, nucleotide triphosphates and required cofactors for the enzymes are provided as a single lyophilized reagent that, when reconstituted, forms a proper reagent for use in the present amplification methods. In these kits, a lyophilized primer reagent may also be provided. In other preferred kits, lyophilized probe reagents are provided.

Typical packaging materials would include solid matrices such as glass, plastic, paper, foil, micro-particles and the like, capable of holding within fixed limits detection probes, helper probes and/or amplification oligonucleotides of the present invention. Thus, for example, the packaging materials can include glass vials used to contain sub-milligram (e.g., picogram or nanogram) quantities of a contemplated probe or primer, or they can be microtiter plate wells to which probes or primers of the present invention have been operatively affixed, i.e., linked so as to be capable of participating in an amplification and/or detection method of the present invention.

The instructions will typically indicate the reagents and/or concentrations of reagents and at least one assay method parameter that might be, for example, the relative amounts of reagents to use per amount of sample. In addition, such specifics as maintenance, time periods, temperature and buffer conditions may also be included.

The diagnostic systems of the present invention contemplate kits having any of the detection probes, helper probes, capture probes and/or amplification oligonucleotides described herein, whether provided individually or in one of the preferred combinations described above, for use in amplifying and/or determining the presence or amount of *T. vaginalis* in a test sample.

EXAMPLES

Examples are provided below illustrating different aspects and embodiments of the invention. It is believed that these examples accurately reflect the details of experiments actually performed, however, it is possible that some minor discrepancies may exist between the work actually performed and the experimental details set forth below which do not affect the conclusions of these experiments. Skilled artisans will appreciate that these examples are not intended to limit the invention to the specific embodiments described therein.

1. Organism Lysis

Whole cells in the examples below were chemically lysed in a transport medium described below in the "Reagents" section. This transport medium is a detergent-containing buffered solution which, in addition to lysing cells, protects released RNAs by inhibiting the activity of RNAses present in a test sample.

2. Oligonucleotide Synthesis

Oligonucleotides featured in the examples below include detection probes, helper probes, primers and capture probes. These oligonucleotides were synthesized using standard phosphoramidite chemistry, various methods of which are well known in the art. See, e.g., Caruthers et al., *Methods in Enzymol.*, 154:287 (1987). Synthesis was performed using an Expedite™ 8909 Nucleic Acid Synthesizer (Applied Biosystems; Foster City, Calif.). The detection probes were also synthesized to include a non-nucleotide linker, as disclosed by Arnold et al. in U.S. Pat. Nos. 5,585,481 and 5,639,604, and labeled with a chemiluminescent acridinium ester, as disclosed by Arnold et al. in U.S. Pat. No. 5,185,439.

3. Transcription-Mediated Amplification

Amplification of a target sequence in the following examples was by a Transcription-Mediated Amplification (TMA) procedure disclosed by, for example, Kacian et al. in U.S. Pat. Nos. 5,399,491 and 5,480,784 and by LEE ET AL., supra, ch. 8. TMA is an isothermal amplification procedure which allows for a greater than one billion-fold increase in copy number of the target sequence using reverse transcriptase and RNA polymerase (see Enzyme Reagents below). A TMA reaction involves converting a single-stranded target sequence to a double-stranded DNA intermediate by reverse transcriptase in the presence of a pair of amplification oligonucleotides, one of which has a 5' RNA polymerase-specific promoter sequence. In this embodiment, the DNA intermediate includes a double-stranded promoter sequence which is recognized by a RNA polymerase and directs transcription of the target sequence into hundreds of copies of RNA. Each of these transcribed RNA molecules, in turn, can be converted to a double-stranded DNA intermediate which is used for producing additional RNA. Thus, the TMA reaction proceeds exponentially. The particulars of the TMA reactions used in the following examples are set forth below.

4. Reagents

Various reagents are identified in the examples below, which include a lysis buffer, a target capture reagent, an amplification reagent, a primer reagent, an enzyme reagent, a hybridization reagent, a selection reagent, and detection reagents. With the exception of Example 1, the formulations and pH values (where relevant) of these reagents were as follows.

Lysis Buffer: The "Lysis Buffer" of the following examples contained 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

Target Capture Reagent: The "Target Capture Reagent" of the following examples contained 250 mM HEPES free acid dihydrate, 310 mM lithium hydroxide monohydrate, 1.88 M lithium chloride, 100 mM EDTA free acid, 2 M lithium hydroxide to pH 6.4, and 250 µg/ml 1 micron magnetic particles Sera-Mag™ MG-CM Carboxylate Modified (Seradyn, Inc.; Indianapolis, Ind.; Cat. No. 24152105-050450) having oligo(dT)$_{14}$ covalently bound thereto.

Wash Solution: The "Wash Solution" of the following examples contained 10 mM HEPES free acid, 6.5 mM sodium hydroxide, 1 mM EDTA free acid, 0.3% (v/v) ethyl alcohol absolute, 0.02% (w/v) methyl paraben, 0.01% (w/v) propyl paraben, 150 mM sodium chloride, 0.1 % (w/v) lauryl sulfate, sodium (SDS), and 4 M sodium hydroxide to pH 7.5.

Amplification Reagent: The "Amplification Reagent" was a lyophilized form of a 3.6 mL solution containing 26.7 mM rATP, 5.0 mM rCTP, 33.3 mM rGTP and 5.0 mM rUTP, 125 mM HEPES free acid, 8% (w/v) trehalose dihydrate, 1.33 mM dATP, 1.33 mM dCTP, 1.33 mM dGTP and 1.33 mM dTTP, and 4 M sodium hydroxide to pH 7.5. The Amplification Reagent was reconstituted in 9.7 mL of the Amplification Reagent Reconstitution Solution described below.

Amplification Reagent Reconstitution Solution: The "Amplification Reagent Reconstitution Solution" contained 0.4% (v/v) ethyl alcohol absolute, 0.10% (w/v) methyl paraben, 0.02% (w/v) propyl paraben, 33 mM KCl, 30.6 mM MgCl$_2$, 0.003% phenol red.

Primer Reagent: The "Primer Reagent" of the following examples contained 1 mM EDTA disodium dihydrate, ACS, 10 mM Trizma® base, and 6M hydrochloric acid to pH 7.5.

Enzyme Reagent: The "Enzyme Reagent" of the following examples was a lyophilized form of a 1.45 mL solution containing 20 mM HEPES free acid dihydrate, 125 mM N-acetyl-L-cysteine, 0.1 mM EDTA disodium dihydrate, 0.2% (v/v) TRITON® X-100 detergent, 0.2 M trehalose dihydrate, 0.90 RTU/mL Moloney murine leukemia virus ("MMLV") reverse transcriptase, and 0.20 U/mL T7 RNA polymerase, and 4M sodium hydroxide to pH 7.0. (One "unit" or "RTU" of activity is defined as the synthesis and release of 5.75 fmol cDNA in 15 minutes at 37° C. for MMLV reverse transcriptase, and for T7 RNA polymerase, one "unit" or "U" of activity is defined as the production of 5.0 fmol RNA transcript in 20 minutes at 37° C.) The Enzyme Reagent was reconstituted in 3.6 mL of the Enzyme Reagent Reconstitution Solution described below.

Enzyme Reagent Reconstitution Solution: The "Enzyme Reagent Reconstitution Solution" of the following examples contained 50 mM HEPES free acid, 1 mM EDTA free acid, 10% (v/v) TRITON® X-100 detergent, 120 mM potassium chloride, 20% (w/v) glycerol anhydrous, and 4 M sodium hydroxide to pH 7.0.

Hybridization Reagent: The "Hybridization Reagent" contained 100 mM succinic acid free acid, 2% (w/v) lithium lauryl sulfate, 100 mM lithium hydroxide monohydrate, 15 mM aldrithiol-2, 1.2 M lithium chloride, 20 mM EDTA free acid, 3.0% (v/v) ethyl alcohol absolute, and 2M lithium hydroxide to pH 4.7.

Selection Reagent: The "Selection Reagent" of the following examples contained 600 mM boric acid, ACS, 182.5 mM sodium hydroxide, ACS, 1% (v/v) TRITON® X-100 detergent, and 4 M sodium hydroxide to pH 8.5.

Detection Reagents: The "Detection Reagents" of the following examples comprised Detect Reagent I, which contained 1 mM nitric acid and 32 mM hydrogen peroxide, 30% (v/v), and Detect Reagent II, which contained 1.5 M sodium hydroxide.

Oil Reagent: The "Oil Reagent" of the following examples was a silicone oil (United Chemical Technologies, Inc., Bristol, Pa.; Cat. No. PS038).

Example 1

Specificity of *T. vaginalis* Direct Detection Assay

In this experiment, we compared the specificity of two detection probes targeting different regions of the 18S rRNA of *T. vaginalis* (ATCC No. 50143) in a non-amplified, direct detection assay. The probes of this experiment were tested alone or in combination with each other and/or a pair of helper probes. For each organism tested, sample tubes were prepared containing two replicates of each of the approximate cell amounts indicated in Table 2 below. The non-target organisms included *Giardia intestinalis* (ATCC No. 30888), *Trimastix pyriformis* (ATCC No. 50562) and *Trichomonas tenax* (ATCC No. 30207). Two replicates each of both a negative control and a *T. vaginalis* rRNA positive control were also included to confirm that the reagents and conditions supported detectable hybridization of the probes to the target sequences and that detectable hybridization would not occur in the absence of the target nucleic acid. The negative control was also used to determine background signal. To lyse the cells and release nucleic acid, the contents of each sample tube were suspended in 300 µL of a lysis buffer (Gen-Probe; Cat. No. 3275 or 3300) and then heated in a 95° C. water bath for about 10 minutes. Following incubation, the samples were cooled at room temperature for about 5 minutes.

Sample tubes were also set up in the tube rack of a magnetic separation unit (Gen-Probe; Cat. No. 1639) and each was provided with 100 µL of a hybridization reagent (3 mM EDTA disodium dihydrate, 3 mM EGTA free acid, 17% (w/v) lithium lauryl sulfate, 190 mM succinic acid free acid, lithium hydroxide monohydrate, and 2 M lithium hydroxide to pH 5.1). The hybridization reagent included one of the probe or probe mix reagents of Table 1 below, where the amount of probe is indicated by reference to an "RLU" or relative light units value, which is a measure of chemiluminescence. For these probe and probe mix reagents, Probe 1 had the base sequence of SEQ ID NO:7 and a standard acridinium ester label joined to the probe by means of a non-nucleotide linker positioned between nucleotides 12 and 13 (reading 5' to 3'), Probe 2 had the base sequence of SEQ ID NO:3 and a standard acridinium ester label joined to the probe by means of a non-nucleotide linker positioned between nucleotides 14 and 15 (reading 5' to 3'), Helper Probe 1 had the base sequence of SEQ ID NO:23, and Helper Probe 2 had the base sequence of SEQ ID NO:27.

TABLE 1

Probe and Probe Mix Reagents

|  | Probe 1 (3 × 10⁶ RLU) | Probe 2 (3 × 10⁶ RLU) | Helper Probe 1 (3 pmol) | Helper Probe 2 (3 pmol) |
|---|---|---|---|---|
| Reagent A | ✓ | ✓ | ✓ | ✓ |
| Reagent B | ✓ |  |  |  |
| Reagent C |  | ✓ |  |  |
| Reagent D |  | ✓ | ✓ | ✓ |

After adding the probe and probe mix reagents, the sample tubes were vortexed for about 10 seconds to ensure homogeneity of the hybridization reagent. The hybridization reagent of each sample tube was combined with 100 µL of lysed material from one of the sample tubes above. The sample tubes were then covered with sealing cards (Gen-Probe; Cat. No.2085) and the rack was hand-shaken several times to mix the contents of the sample tubes prior to incubating the sample tubes in a 60° C. water bath for about 1 hour.

The tube rack was removed from the water bath and the sealing cards were removed from the sample tubes before adding 1 mL of a separation suspension to each sample tube. The separation suspension was a 20:1 mixture of a selection reagent (222 mM 6N hydrochloric acid solution, 190 mM sodium tetraborate, 0.01% (v/v) gelatin (fish skin), and 6.43% (v/v) TRITON® X-102 detergent) and a separation reagent (1 mM EDTA disodium dihydrate, 0.02% (w/v) sodium azide and 1.25 mg/mL BioMag® particles (Polysciences, Inc., Warrington, Pa.; Cat. No. 8-4100T). The sample tubes were again covered with sealing cards and the tube rack was vigorously shaken 3 to 5 times to mix the contents before placing it in a 60° C. water bath for about 10 minutes to immobilize nucleic acid present in the sample tubes on the BioMag particles. The tube rack was removed from the water bath and the tube rack was placed on the base of the magnetic separation unit for 5 minutes at room temperature to magnetically isolate the BioMag particles. With the sealing cards removed, the tube rack and base of the magnetic separation unit were inverted to decant the supernatants of the sample tubes. To remove residual liquid, the magnetic separation unit was then shaken 2 to 3 times and the sample tubes were blotted 3 times for 5 seconds on absorbent paper. Each sample tube was then filled to the rim with a wash solution (25 mM sodium hydroxide, 20 mM sodium tetraborate, 0.1% (w/v) Zwittergent® 3-14 detergent, and 4M sodium hydroxide to pH 10.4) and allowed to remain on the base of the magnetic separation unit for 20 minutes at room temperature. Holding the tube rack and base of the magnetic separation unit together, the supernatants were decanted and the magnetic separation unit was shaken 2 to 3 times. The tubes were returned to their upright position, leaving about 50 to 100 µL of the wash solution in each sample tube, and the tube rack was separated from the base of the magnetic separation unit. The sample tubes were then analyzed in a LEADER® 450h or a LEADER® HC+Luminometer equipped with automatic injection of Detection Reagent 1, followed by automatic injection of Detection Reagent 2. An RLU value of 1000 was determined to be the cut-off for a negative result.

The results are summarized in Table 2 below and indicate that the probes and probe mixes tested in this experiment were specific for *T. vaginalis*.

TABLE 2

Specificity of *T. vaginalis* Direct Detection Assay

| Sample | Cell Count | Avg. RLU | | | |
|---|---|---|---|---|---|
|  |  | Reagent A | Reagent B | Reagent C | Reagent D |
| *Giardia intestinalis* | 2 × 10⁵ | −189 | 170 | 58 | 315 |
|  | 2 × 10⁴ | 191 | −10 | 328 | −31 |
| *Trimastix pyriformis* | 1 × 10⁵ | 31 | −186 | 453 | −128 |
|  | 1 × 10⁴ | −120 | −26 | 266 | −146 |
| *Trichomonas tenax* | 4.9 × 10⁵ | −243 | 328 | 52 | 320 |
|  | 4.9 × 10⁴ | −127 | 126 | 14 | 137 |
| *Trichomonas vaginalis* | 2 × 10⁵ | 636,638 | 298,244 | 25,439 | 356,041 |
|  | 2 × 10⁴ | 407,087 | 53,470 | 5,165 | 299,776 |
| Positive Control | 10.5 ng RNA | 85,274 | 7,317 | 2,506 | 55,597 |
| Negative Control | N/A | 282 | 219 | 36 | 651 |

Example 2

Sensitivity and Specificity of *T. vaginalis* Amplification Assay

This experiment was conducted to determine the sensitivity and specificity of an amplification assay targeting 18S rRNA of *T. vaginalis* (ATCC No.50143) in the presence of several closely-related, non-target organisms. The non-target organisms in this experiment included *Giardia intestinalis* (ATCC No. 30888), *Trimastix pyriformis* (ATCC No. 50562) and *Trichomonas tenax* (ATCC No. 30207), the latter being the most closely related to *T. vaginalis*. Sample tubes were prepared in replicates of four for each organism at each of the approximate cell concentrations indicated in Table 2 below. Two replicates each of a *T. vaginalis* RNA positive control (5 fg/replicate) and a negative control were also prepared. To lyse the cells and release target nucleic acid, 400 µL of the Lysis Buffer was added to each sample tube, and the sample tubes were heated for about 10 minutes in a 95° C. water bath. Following incubation, the samples were cooled at room temperature for about 5 minutes.

To separate *T. vaginalis* target nucleic acid from other components present in the sample tubes, the contents of the sample tubes were transferred to the reaction tubes of Ten-Tube Units (Gen-Probe; Cat. No. TU0022) and combined with 100 µL of the Target Capture Reagent containing 3 pmol of a target capture probe having the sequence of: SEQ ID NO:99 gcctgctgctacccgtggatattt-taaaaaaaaaaaaaaaaaaaaaaaaaaaaaa. This capture probe includes a 5' target binding region (SEQ ID NO:31) and a 3' immobilized probe binding region (SEQ ID NO:98). The TTUs were covered with a sealing card (Gen-Probe; Cat. No. 2085), hand-shaken, incubated in a 62° C. water bath for about 30 minutes to permit hybridization of the target binding region of the capture probe to the target nucleic acid, and cooled at room temperature for about 30 minutes to facilitate hybridization of the oligo(dA)$_{30}$ sequence of the immobilized probe binding region of the capture probe to oligo(dT)$_{14}$ bound to the magnetic particles. Following cooling of the samples, a DTS™ 1600 Target Capture System (Gen-Probe; Cat. No. 5202) was used to isolate and wash the magnetic particles. The DTS 1600 Target Capture System has a test tube bay for positioning TTUs and applying a magnetic field thereto. The TTUs were placed in the test tube bay on the DTS™ 1600 Target Capture System for about 5 minutes in the presence of the magnetic field to isolate the magnetic particles within the reaction tubes, after which the sample solutions were aspirated from the TTUs. Each tube was then provided with 1 mL of the Wash Solution, covered with a sealing card and vortexed for 10 to 20 seconds to resuspend the magnetic particles. The TTUs were returned to the test tube bay on the DTS™ 1600 Target Capture System and allowed to stand at room temperature for about 5 minutes before the wash solution was aspirated.

Following the target capture step, 75 µL of the reconstituted Amplification Reagent spiked with a pair of primers was added to each of the reaction tubes. Each primer was present at a concentration of 15 pmol in the spiked Amplification Reagent. (It is noted that 4 pmol of each primer per reaction mixture is currently preferred.) The primers for this experiment included a primer having the base sequence of SEQ ID NO:45 and a promoter-primer having the base sequence of SEQ ID NO:100 aatttaatacgactcactatagggagag-gcatcacggacctgttattgc. The promoter primer included a 3' target-binding portion (SEQ ID NO:55) and a 5' T7 promoter sequence (SEQ ID NO:89). The reaction tubes were then provided with 200 µL of the Oil Reagent, covered with a sealing card, and vortexed for about 10 seconds before being incubated in a 62° C. water bath for about 10 minutes for an initial anneal step to promote binding of the promoter-primers to the target nucleic acid. The reaction tubes were transferred to a 42° C. water bath for about 5 minutes, the sealing cards were removed from the reaction tubes, and 25 µL of the reconstituted Enzyme Reagent was added to each of the reaction tubes. The reaction tubes were again covered with a sealing card, removed from the water bath, and their contents were gently mixed by hand. After mixing, the reaction tubes were again incubated in the 42° C. water bath for about 60 minutes.

For detection of *T. vaginalis* amplification products, the reaction tubes were removed from the water bath and 100 µL of the Hybridization Reagent containing 100 fmol of a detection probe was added to each reaction tube. The detection probe had the base sequence of SEQ ID NO:3 and a standard acridinium ester label joined to the probe by means of a non-nucleotide linker positioned between nucleotides 17 and 18, reading 5' to 3'. The reaction tubes were covered with a sealing card and vortexed for about 10 seconds before being incubated in a 62° C. water bath for about 20 minutes to allow hybridization of the detection probe to amplification products present in the reaction tubes. The reaction tubes were then removed from the water bath and allowed to cool at room temperature for about 5 minutes before adding 250 µL of the Selection Reagent to each reaction tube. The reaction tubes were covered with a sealing card and vortexed for about 10 seconds before being incubated in a 62° C. water bath for about 10 minutes to hydrolyze acridinium ester labels associated with unhybridized probe. The reaction tubes were then cooled in a 18° to 28° C. water bath for about 15 minutes before being analyzed in a LEADER® 450h or a LEADER® HC+ Luminometer equipped with automatic injection of Detection Reagent 1, followed by automatic injection of Detection Reagent 2. The cut-off for a negative result in this experiment was 50,000 RLU.

The results are summarized in Table 3 below and indicate that the *T. vaginalis* assay of this experiment amplified and detected *T. vaginalis*-derived nucleic acid without cross-reacting with nucleic acid derived from *Giardia lamblia*, *Trimastix pyriformis* or *Trichomonas tenax*. As above, the term "RLU" in this table stands for relative light units, and the term "CV" stands for coefficient of variation and represents the standard deviation of the replicates over the mean of the replicates as a percentage.

TABLE 3

Sensitivity and Specificity of the *T. vaginalis* Amplification Assay

| Sample | Cell Count | Avg. RLU | % CV |
|---|---|---|---|
| Giardia | $4 \times 10^4$ | 2925 | 9 |
| lamblia | $4 \times 10^3$ | 2882 | 16 |
|  | $4 \times 10^2$ | 3100 | 28 |
| Trimastix | $4 \times 10^5$ | 3322 | 14 |
| pyriformis | $4 \times 10^4$ | 2720 | 7 |
|  | $4 \times 10^3$ | 2769 | 19 |
| Trichomonas | $4 \times 10^4$ | 2473 | 18 |
| tenax | $4 \times 10^3$ | 4613 | 71 |
|  | $4 \times 10^2$ | 2315 | 7 |
| Trichomonas | $4 \times 10^4$ | 2,362,258 | 59 |
| vaginalis | $4 \times 10^3$ | 1,427,954 | 46 |
|  | $4 \times 10^2$ | 2,754,667 | 31 |
| Positive Control | N/A | 4,359,224 | 2 |
| Negative Control | N/A | 5122 | 47 |

Example 3

Primer Sets for Use in a *T. vaginalis* Amplification Assay Directed to the 400 Region of *T. vaginalis* 18S rRNA The purpose of this experiment was to compare the amplification efficiency of various primer sets for amplifying a portion of the 400 region of a transcript derived from the 18S rRNA of *T. vaginalis* at different initial annealing temperatures. The amplification and detection procedures of this experiment were identical to those of Example 2 above, except that one group of primer sets was exposed to an 95° C. initial annealing step instead of a 62° C. initial annealing step after the Oil Reagent was added to the sample tubes. Because the primer sets of this experiment targeted transcript, a target capture step was not included.

The detection probe used for detecting the formation of amplification products in this experiment had the base sequence of SEQ ID NO:9 and a standard acridinium ester label joined to the probe by means of a non-nucleotide linker positioned between nucleotides 17 and 18, reading 5' to 3'. Primers 1-3 identified in Tables 3 and 4 below had the base sequences of SEQ ID Nos. 61, 65 and 69, respectively. And Primers 4-6 identified in Tables 3 and 4 below were promoter-primers having the following base sequences:

Primer 4: aatttaatacgactcactatagggagac-ctctgctaggtttcggtacggt (SEQ ID NO:101),

Primer 5: aatttaatacgactcactatagg-gagagactggccctctgctaggtttcg (SEQ ID NO:102), and Primer 6: aatttaatacgactcactatagg-gagagctgctggcaccagactgg (SEQ ID NO:103).

Primers 4-6 had a 5' promoter sequence (SEQ ID NO:89) and 3' target binding portions having the base sequences of SEQ ID Nos. 79, 83 and 87, respectively.

The results are summarized in Tables 4 and 5 below and indicate that the primer set of Primers 3 and 5 performed the best at amplifying the target region under both sets of conditions. The results also indicate that in most instances, the amplification efficiency of the primer sets was better with a 95° C. rather than a 62° C. initial annealing step. As above, the term "RLU" in these tables stands for relative light units, and the term "CV" stands for coefficient of variation.

TABLE 4

Primer Sets for *T. vaginalis* rRNA Amplification
Employing a 62° C. Initial Annealing Step

| Primer Set | Copy Number | Avg. RLU | % CV |
|---|---|---|---|
| Primers 3 and 4 | $1.5 \times 10^4$ | 41,788 | 30 |
|  | 1,875 | 30,053 | 23 |
| Primers 3 and 5 | $1.5 \times 10^4$ | 53,763 | 10 |
|  | 1,875 | 46,493 | 13 |
| Primers 1 and 6 | $1.5 \times 10^4$ | 3,619 | 4 |
|  | 1,875 | 3,176 | 4 |
| Primers 2 and 6 | $1.5 \times 10^4$ | 28,059 | 43 |
|  | 1,875 | 11,758 | 90 |
| Primers 3 and 6 | $1.5 \times 10^4$ | 46,365 | 12 |
|  | 1,875 | 6,646 | 13 |

TABLE 5

Primer Sets for *T. vaginalis* rRNA Amplification
Employing a 95° C. Initial Annealing Step

| Primer Set | Copy Number | Avg. RLU | % CV |
|---|---|---|---|
| Primers 3 and 4 | $1.5 \times 10^4$ | 59,660 | 22 |
|  | 1,875 | 40,248 | 15 |
| Primers 3 and 5 | $1.5 \times 10^4$ | 85,698 | 53 |
|  | 1,875 | 45,099 | 12 |
| Primers 1 and 6 | $1.5 \times 10^4$ | 5,553 | 65 |
|  | 1,875 | 11,286 | 157 |
| Primers 2 and 6 | $1.5 \times 10^4$ | 20,033 | 47 |
|  | 1,875 | 17,104 | 47 |
| Primers 3 and 6 | $1.5 \times 10^4$ | 40,969 | 8 |
|  | 1,875 | 13,323 | 46 |

Example 4

Primer Sets for Use in a *T. vaginalis* Amplification Assay Directed to the 1100 Region of *T. vaginalis* 18S rRNA The purpose of this experiment was to compare the amplification efficiency of several primer sets for amplifying a portion of the 1100 region of a transcript derived from the 18S rRNA of *T. vaginalis*. The amplification and detection procedures of this experiment were identical to those of Example 2 above. A target capture step was not included.

The detection probe used for detecting the formation of amplification products in this experiment had the base sequence of SEQ ID NO:3 and a standard acridinium ester label joined to the probe by means of a non-nucleotide linker positioned between nucleotides 17 and 18, reading 5' to 3'. Primers 1 and 2 identified in Table 5 below had the base sequences of SEQ ID Nos. 41 and 45, respectively. And Primers 3 and 4 identified in Tables 6 below were promoter-primers having the following base sequences:

Primer 3: aatttaatacgactcactatagggagac-ctcttccacctgctaaaatcgcag (SEQ ID NO:104), and Primer 4: aatttaatacgactcactatagggagag-gcatcacggacctgttattgc (SEQ ID NO:105).

Primers 3 and 4 had a 5' promoter sequence (SEQ ID NO:89) and 3' target binding portions having the base sequences of SEQ ID Nos. 51 and 55, respectively.

The results are summarized in Table 6 below and indicate that primer sets which included the promoter-primer of SEQ ID NO:105 (Primer 4) were superior at amplifying the target region. As above, the term "RLU" in this table stands for relative light units, and the term "CV" stands for coefficient of variation.

TABLE 6

Primer Sets for *T. vaginalis* rRNA Amplification

| Primer Set | Copy Number | Avg. RLU | % CV |
|---|---|---|---|
| Primers 1 and 3 | $1.5 \times 10^4$ | 306,917 | 4 |
|  | 1,875 | 130,842 | 10 |
| Primers 1 and 4 | $1.5 \times 10^4$ | 5,262,130 | 1 |
|  | 1,875 | 4,584,780 | 1 |
| Primers 2 and 3 | $1.5 \times 10^4$ | 169,767 | 6 |
|  | 1,875 | 27,693 | 16 |
| Primers 2 and 4 | $1.5 \times 10^4$ | 5,193,952 | 3 |
|  | 1,875 | 5,049,133 | 1 |

Example 5

Sensitivity of *T. vaginalis* Amplification Assay

This experiment was designed to evaluate the sensitivity of an amplification assay targeting a portion of the 1100 region of 18S rRNA of *T. vaginalis* present in a transcript derived from *T. vaginalis* nucleic acid following the procedures and employing the detection probe and Primers 2 and 4 of Example 4 above. The results of this experiment are summarized in Table 7 below and indicate at least about 19 copy sensitivity (one of the replicates had a total RLU of about 300,000, the cut-off for a positive result in this assay). As above, the term "RLU" in this table stands for relative light units, and the term "CV" stands for coefficient of variation. The CV values are generally larger with lower concentrations of transcript because some of the replicates are being amplified, while others were not, thereby resulting in a higher standard deviation between the replicates.

TABLE 7

Varying Concentrations of Transcript in *T. vaginalis* Amplification Assay

| Copy Number | Avg. RLU | % CV |
|---|---|---|
| 20,000 | 5,182,728 | 2 |
| 10,000 | 5,163,317 | 2 |
| 5000 | 5,400,837 | 3 |
| 2500 | 5,360,159 | 1 |
| 1250 | 5,371,082 | 4 |
| 625 | 5,242,293 | 2 |
| 312 | 5,098,105 | 2 |
| 156 | 5,017,485 | 2 |
| 78 | 4,831,400 | 2 |
| 39 | 4,661,045 | 5 |
| 19 | 2,908,561 | 63 |
| 0 | 2695 | 4 |

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

What we claim is:

1. A detection probe for use in determining the presence of *Trichomonas vaginalis* in a test sample, said probe comprising a target binding region consisting of the base sequence of SEQ ID NO:1, SEQ ID NO:2, SEQ ID NO:3 or SEQ ID NO:4, wherein said probe forms a hybrid stable for detection with nucleic acid derived from *Trichomonas vaginalis* but not from *Trichomonas tenax* under assay conditions which include a temperature of about 60° C. and a salt concentration of about 0.6 M to about 0.9 M, and wherein said probe does not include bases in addition to the bases of said target binding region which participate in stable hybridization with *Trichomonas vaginalis* derived nucleic acid under said assay conditions.

2. The probe of claim 1, wherein the base sequence of said probe consists of the base sequence of SEQ ID NO:1, SEQ ID NO:2, SEQ ID NO:3 or SEQ ID NO:4.

3. The probe of claim 1, wherein said probe is a self-hybridizing probe under said assay conditions and in the absence of nucleic acid derived from *Trichomonas vaginalis*.

4. The probe of claim 3, wherein said probe comprises a pair of interacting labels.

5. The probe of claim 1, wherein said probe is up to 50 bases in length.

6. The probe of claim 1, wherein said probe comprises a detectable label.

7. The probe of claim 1, wherein said target binding region includes at least one ribonucleotide modified to include a 2'-O-methyl substitution to the ribofuranosyl moiety or a pseudo peptide backbone joins at least a portion of the bases of said target binding region.

8. A composition comprising said probe of claim 1 hybridized to nucleic acid derived from *Trichomonas vaginalis*.

9. A probe mix comprising said probe of claim 1 and a helper probe.

10. The probe mix of claim 9, wherein the base sequence of said helper probe consists of the base sequence of SEQ ID NO:21, SEQ ID NO:22, SEQ ID NO:23, SEQ ID NO:24, SEQ ID NO:25, SEQ ID NO:26, SEQ ID NO:27 or SEQ ID NO:28.

11. A method for determining the presence of *Trichomonas vaginalis*, said method comprising the steps of:
   a) contacting a test sample with said probe of claim 1; and
   b) determining whether said hybrid has formed as indication of the presence of *Trichomonas vaginalis* in said test sample.

12. A detection probe for use in determining the presence of *Trichomonas vaginalis* in a test sample, said probe comprising a target binding region consisting of or contained within the base sequence of SEQ ID NO:5, SEQ ID NO:6, SEQ ID NO:7 or SEQ ID NO:8, wherein said probe forms a hybrid stable for detection with nucleic acid derived from *Trichomonas vaginalis* but not from *Trichomonas tenax* under assay conditions which include a temperature of about 60° C. and a salt concentration of about 0.6 M to about 0.9 M, and wherein said probe does not include bases in addition to the bases of said target binding region which participate in stable hybridization with *Trichomonas vaginalis* derived nucleic acid under said assay conditions.

13. The probe of claim 12, wherein the base sequence of said probe consists of or is contained within the base sequence of SEQ ID NO:5, SEQ ID NO:6, SEQ ID NO:7 or SEQ ID NO:8.

14. The probe of claim 12, wherein the base sequence of said probe consists of the base sequence of SEQ ID NO:5, SEQ ID NO:6, SEQ ID NO:7 or SEQ ID NO:8.

15. The probe of claim 12, wherein said probe is a self-hybridizing probe under said assay conditions and in the absence of nucleic acid derived from *Trichomonas vaginalis*.

16. The probe of claim 15, wherein said probe comprises a pair of interacting labels.

17. The probe of claim 12, wherein said probe is up to 50 bases in length.

18. The probe of claim 12, wherein said probe comprises a detectable label.

19. The probe of claim 12, wherein said target binding region includes at least one ribonucleotide modified to include a 2'-O-methyl substitution to the ribofuranosyl moiety or a pseudo peptide backbone joins at least a portion of the bases of said target binding region.

20. A composition comprising said probe of claim 12 hybridized to nucleic acid derived from *Trichomonas vaginalis*.

21. A method for determining the presence of *Trichomonas vaginalis*, said method comprising the steps of:
   a) contacting a test sample with said probe of claim 12; and
   b) determining whether said hybrid has formed as indication of the presence of *Trichomonas vaginalis* in said test sample.

22. A detection probe for use in determining the presence of *Trichomonas vaginalis* in a test sample, said probe comprising a target binding region consisting of or contained within the base sequence of SEQ ID NO:9, SEQ ID NO:10, SEQ ID NO:11 or SEQ ID NO:12, wherein said probe forms a hybrid stable for detection with nucleic acid derived from *Trichomonas vaginalis* but not from *Trichomonas tenax* under assay conditions which include a temperature of about 60° C. and a salt concentration of about 0.6 M to about 0.9 M, and wherein said probe does not include bases in addition to the bases of said target binding region which participate in stable hybridization with *Trichomonas vaginalis* derived nucleic acid under said assay conditions.

23. The probe of claim 22, wherein the base sequence of said probe consists of or is contained within the base sequence of SEQ ID NO:9, SEQ ID NO:10, SEQ ID NO:11 or SEQ ID NO:12.

24. The probe of claim 22, wherein the base sequence of said probe consists of the base sequence of SEQ ID NO:9, SEQ ID NO:10, SEQ ID NO:11 or SEQ ID NO:12.

25. The probe of claim 22, wherein said probe is a self-hybridizing probe under said assay conditions and in the absence of nucleic acid derived from *Trichomonas vaginalis*.

26. The probe of claim 25, wherein said probe comprises a pair of interacting labels.

27. The probe of claim 22, wherein said probe is up to 50 bases in length.

28. The probe of claim 22, wherein said probe comprises a detectable label.

29. The probe of claim 22, wherein said target binding region includes at least one ribonucleotide modified to include a 2'-O-methyl substitution to the ribofuranosyl moiety or a pseudo peptide backbone joins at least a portion of the bases of said target binding region.

30. A composition comprising said probe of claim 22 hybridized to nucleic acid derived from *Trichomonas vaginalis*.

31. A method for determining the presence of *Trichomonas vaginalis*, said method comprising the steps of:
   a) contacting a test sample with said probe of claim 22; and
   b) determining whether said hybrid has formed as indication of the presence of *Trichomonas vaginalis* in said test sample.

32. A detection probe for use in determining the presence of *Trichomonas vaginalis* in a test sample, said probe comprising a target binding region consisting of or contained within the base sequence of SEQ ID NO:13, SEQ ID NO:14, SEQ ID NO:15 or SEQ ID NO:16, wherein said probe forms a hybrid stable for detection with nucleic acid derived from *Trichomonas vaginalis* but not from *Trichomonas tenax* under assay conditions which include a temperature of about 60° C. and a salt concentration of about 0.6 M to about 0.9 M, and wherein said probe does not include bases in addition to the bases of said target binding region which participate in stable hybridization with *Trichomonas vaginalis* derived nucleic acid under said assay conditions.

33. The probe of claim 32, wherein the base sequence of said probe consists of or is contained within the base sequence of SEQ ID NO: 13, SEQ ID NO: 14, SEQ ID NO: 15 or SEQ ID NO:16.

34. The probe of claim 32, wherein the base sequence of said probe consists of the base sequence of SEQ ID NO:13, SEQ ID NO:14, SEQ ID NO:15 or SEQ ID NO:16.

35. The probe of claim 32, wherein said probe is a self-hybridizing probe under said assay conditions and in the absence of nucleic acid derived from *Trichomonas vaginalis*.

36. The probe of claim 35, wherein said probe comprises a pair of interacting labels.

37. The probe of claim 32, wherein said probe is up to 50 bases in length.

38. The probe of claim 32, wherein said probe comprises a detectable label.

39. The probe of claim 32, wherein said target binding region includes at least one ribonucleotide modified to include a 2'-O-methyl substitution to the ribofuranosyl moiety or a pseudo peptide backbone joins at least a portion of the bases of said target binding region.

40. A composition comprising said probe of claim 32 hybridized to nucleic acid derived from *Trichomonas vaginalis*.

41. A method for determining the presence of *Trichomonas vaginalis*, said method comprising the steps of:
   a) contacting a test sample with said probe of claim 32; and
   b) determining whether said hybrid has formed as indication of the presence of *Trichomonas vaginalis* in said test sample.

* * * * *